(12) United States Patent
Furukawa

(10) Patent No.: US 7,858,346 B2
(45) Date of Patent: Dec. 28, 2010

(54) REGENERATION AND NEOGENESIS OF RETINAL VISUAL CELL-EXPRESSING OTX2 PROTEIN

(75) Inventor: Takahisa Furukawa, Suita (JP)

(73) Assignee: Japan Science Technology Agency, Saitama (JP)

(*) Notice: Subject to any disclaimer, the term of this patent is extended or adjusted under 35 U.S.C. 154(b) by 0 days.

(21) Appl. No.: 10/542,248

(22) PCT Filed: Feb. 2, 2004

(86) PCT No.: PCT/JP2004/001023

§ 371 (c)(1),
(2), (4) Date: Aug. 16, 2005

(87) PCT Pub. No.: WO2004/069268

PCT Pub. Date: Aug. 19, 2004

(65) Prior Publication Data

US 2006/0122111 A1    Jun. 8, 2006

(30) Foreign Application Priority Data

Feb. 3, 2003  (JP) .............................. 2003-026353

(51) Int. Cl.
C12P 21/04 (2006.01)
C12N 15/85 (2006.01)
C12N 15/63 (2006.01)
C12N 5/00 (2006.01)
C12N 15/11 (2006.01)
C07K 14/00 (2006.01)

(52) U.S. Cl. ................... 435/70.3; 435/325; 435/320.1; 435/377; 530/350; 536/23.1

(58) Field of Classification Search ........................ None
See application file for complete search history.

(56) References Cited

U.S. PATENT DOCUMENTS 6,284,539 B1 * 9/2001 Bowen et al. ............... 435/455

FOREIGN PATENT DOCUMENTS

| CN | 1342666 | 4/2002 |
|---|---|---|
| CN | 1342679 | 4/2002 |
| JP | 2002-325571 | 11/2002 |
| WO | 99/25721 | 5/1999 |
| WO | 99/55838 | 11/1999 |
| WO | WO 0157190 A2 * | 8/2001 |

OTHER PUBLICATIONS

Wells, Biochemistry 29:8509-8517, 1990.*
Ngo et al., The Protein Folding Problem and Tertiary Structure Prediction, pp. 492-495, 1994.*
Bork, Genome Research 10:398-400, 2000.*
Skolnick et al., Trends in Biotech. 18(1):34-39, 2000.*
Doerks et al., Trends in Genetics 14:248-250, 1998.*
Smith et al., Nature Biotechnology 15:1222-1223, 1997.*
Brenner, Trends in Genetics 15:132-133, 1999.*
Bork et al., Trends in Genetics 12:425-427, 1996.*
Baas et al. Brain Res Mol Br Res 78: 26-37, 2000.*
Bobola et al. Mech Development 82: 165-169, 1998.*
Kenyon et al. Dev Biol 240: 77-91, 2001.*
Furukawa et al. Cell 91: 531-541, 1997.*
Ragge et al. Am J Hum Gen 76: 1008-1022, 2005.*
Jacobson et al. Invest Opthal Vis Sci 39: 2417-2426, 1998.*
Freund et al. Cell 91: 543-553, 1997.*
P. Bovolenta et al., "Implication of OTX2 in Pigment Epithelium Determination and Neural Retina Differentiation", The Journal of Neuroscience, vol. 17, No. 11, pp. 4243-4252, Jun. 1, 1997.
S. Sakami et al., "Transcription factor, Otx2, is expressed in regenerating new retina as in the developing retina", Comparative Biochemistry and Physiology Part A Molecular and Integrative Physiology, vol. 130A, No. 4, pp. 874, 109, 2001.
S. Sakami et al., "Expression of Otx2 druing regeneration and development of new retina", Zoological Science, vol. 18, No. Supplement, pp. 64, 0319, 2001.
K. Kastury et al., "Chromosome Locations of Human *EMX* and *OTX* Genes", Genomics, vol. 22, No. 1, pp. 41-45, 1994.
A. Simeone et al., "Nested expression domains of four homeobox genes in developing rostral brain", Letters to Nature, vol. 358, No. 6388, pp. 687-690, 1992.
A. Nishida et al., "Otx2 homeobox gene controls retinal photoreceptor cell fate and pineal gland development", Nature Neuroscience, vol. 6, No. 12, pp. 1255-1263, Dec. 2003.
Nagao, Tomoko, et al., "Developmental Rescue of *Drosophila* Cephalic Defects by the Human *Otx* Genes," Proc. Natl. Acad. Sci. USA, vol. 95, pp. 3737-3742, Mar. 1998.
J. R. Martinez-Morales et al., "Otx Genes Are Required For Tissue Specification in the Developing Eye," Development, 2001, vol. 128, pp. 2019-2030.
Supplementary Partial European Search Report issued Aug. 4, 2009 in corresponding European Patent Application No. 04 70 7324.
D. Bass et al., "Otx2 and mouse retina development", *Development Growth and Differentiation* (2001), vol. 43, No. Supplement, p. S78.
I. Yajima et al., "Functional analysis of Otx2 gene in retinal pigmented epithelial (RPE) cells of the chick embryo", *Pigment Cell Research* (2002), vol. 15, No. Supplement 9, pp. 73-74.

(Continued)

*Primary Examiner*—Jeffrey Stucker
*Assistant Examiner*—Aditi Dutt
(74) *Attorney, Agent, or Firm*—Wenderoth, Lind & Ponack, L.L.P.

(57) ABSTRACT

The present invention provides a medicine, comprising (a) an Otx2 protein or its partial peptide, or a salt thereof, or (b) a DNA or an RNA encoding an Otx2 protein or its partial peptide. The present medicine is useful as an agent for preventing, treating or suppressing progression of a retinal disease including retinal degeneration. In addition, the present medicine is useful, for example, as an agent for inducing differentiation from a retinal stem cell into a retinal photoreceptor cell, in the transplantation of a cell into the retina of patients suffering from retinal diseases.

6 Claims, 4 Drawing Sheets

OTHER PUBLICATIONS

K. Takeda et al., "OTX2 regulates expression of DOP Achrome tautomerase in human retinal pigment epithelium", *Biochemical and Biophysical Research Communications* (2003), vol. 300, No. 4, pp. 908-914.

N. Bobola et al., "OTX2 homeodomain protein binds a DNA element necessary for interphotoreceptor retinoid binding protein gene expression", *Mechanisms of Development* (1998), vol. 82, No. 1-2, pp. 165-169.

* cited by examiner

US 7,858,346 B2

SEQUENCE LISTING

<160> NUMBER OF SEQ ID NOS: 6

<210> SEQ ID NO 1
<211> LENGTH: 297
<212> TYPE: PRT
<213> ORGANISM: Homo sapiens

<400> SEQUENCE: 1

```
Met Met Ser Tyr Leu Lys Gln Pro Pro Tyr Ala Val Asn Gly Leu Ser
  1               5                  10                  15

Leu Thr Thr Ser Gly Met Asp Leu Leu His Pro Ser Val Gly Tyr Pro
                 20                  25                  30

Gly Pro Trp Ala Ser Cys Pro Ala Ala Thr Pro Arg Lys Gln Arg Arg
             35                  40                  45

Glu Arg Thr Thr Phe Thr Arg Ala Gln Leu Asp Val Leu Glu Ala Leu
         50                  55                  60

Phe Ala Lys Thr Arg Tyr Pro Asp Ile Phe Met Arg Glu Glu Val Ala
 65                  70                  75                  80

Leu Lys Ile Asn Leu Pro Glu Ser Arg Val Gln Val Trp Phe Lys Asn
                 85                  90                  95

Arg Arg Ala Lys Cys Arg Gln Gln Gln Gln Gln Gln Asn Gly Gly
            100                 105                 110

Gln Asn Lys Val Arg Pro Ala Lys Lys Lys Thr Ser Pro Ala Arg Glu
        115                 120                 125

Val Ser Ser Glu Ser Gly Thr Ser Gly Gln Phe Thr Pro Pro Ser Ser
130                 135                 140

Thr Ser Val Pro Thr Ile Ala Ser Ser Ala Pro Val Ser Ile Trp
145                 150                 155                 160

Ser Pro Ala Ser Ile Ser Pro Leu Ser Asp Pro Leu Ser Thr Ser Ser
                165                 170                 175

Ser Cys Met Gln Arg Ser Tyr Pro Met Thr Tyr Thr Gln Ala Ser Gly
            180                 185                 190

Tyr Ser Gln Gly Tyr Ala Gly Ser Thr Ser Tyr Phe Gly Gly Met Asp
        195                 200                 205

Cys Gly Ser Tyr Leu Thr Pro Met His His Gln Leu Pro Gly Pro Gly
    210                 215                 220

Ala Thr Leu Ser Pro Met Gly Thr Asn Ala Val Thr Ser His Leu Asn
225                 230                 235                 240

Gln Ser Pro Ala Ser Leu Ser Thr Gln Gly Tyr Gly Ala Ser Ser Leu
                245                 250                 255

Gly Phe Asn Ser Thr Thr Asp Cys Leu Asp Tyr Lys Asp Gln Thr Ala
            260                 265                 270

Ser Trp Lys Leu Asn Phe Asn Ala Asp Cys Leu Asp Tyr Lys Asp Gln
        275                 280                 285

Thr Ser Ser Trp Lys Phe Gln Val Leu
        290                 295
```

<210> SEQ ID NO 2
<211> LENGTH: 2209
<212> TYPE: DNA
<213> ORGANISM: Homo sapiens

<400> SEQUENCE: 2

```
gagagcggga ccggcctcag ctccaacaca gcctccactg tgattaaaaa taaaaattgc    60
```

-continued

| | |
|---|---|
| tagagcagcc ctcactcgcc acatctactt tgatagctgg ctatttggaa tttaaaggat | 120 |
| atttgacttt ttctaacctc ccatgaggct gtaagttcca ctgctccaaa cccacccacc | 180 |
| aaggactctg aacctgtcca ccccgggcgc atcaagatct tccagctggg taccccgat | 240 |
| ttgggccgac tttgcacctc caaacaacct tagcatgatg tcttatctta agcaaccgcc | 300 |
| ttacgcagtc aatgggctga gtctgaccac ttcgggtatg gacttgctgc acccctccgt | 360 |
| gggctacccg gggccctggg cttcttgtcc cgcagccacc ccccggaaac agcgccggga | 420 |
| gaggacgacg ttcactcggg cgcagctaga tgtgctggaa gcactgtttg ccaagacccg | 480 |
| gtacccagac atcttcatgc gagaggaggt ggcactgaaa atcaacttgc ccgagtcgag | 540 |
| ggtgcaggta tggtttaaga atcgaagagc taagtgccgc aacaacagc aacaacagca | 600 |
| gaatggaggt caaacaaag tgagacctgc aaaaagaag acatctccag ctcgggaagt | 660 |
| gagttcagag agtggaacaa gtggccaatt cactccccc tctagcacct cagtcccgac | 720 |
| cattgccagc agcagtgctc ctgtgtctat ctggagccca gcttccatct ccccactgtc | 780 |
| agatcccttg tccacctcct cttcctgcat gcagaggtcc tatcccatga cctatactca | 840 |
| ggcttcaggt tatagtcaag gatatgctgg ctcaacttcc tactttgggg gcatggactg | 900 |
| tggatcatat ttgacccta tgcatcacca gcttcccgga ccaggggcca cactcagtcc | 960 |
| catgggtacc aatgcagtca ccagccatct caatcagtcc ccagcttctc tttccaccca | 1020 |
| gggatatgga gcttcaagct gggttttaa ctcaaccact gattgcttgg attataagga | 1080 |
| ccaaactgcc tcctggaagc ttaacttcaa tgctgactgc ttggattata agatcagac | 1140 |
| atcctcgtgg aaattccagg ttttgtgaag acctgtagaa cctctttttg tgggtgattt | 1200 |
| ttaaatatac tgggctggac attccagttt tagccaggca ttggttaaaa gagttagatg | 1260 |
| ggatgatgct cagactcatc tgatcaaagt tccgagaggc atagaaggaa aaacgaaggg | 1320 |
| ccttagaggg gcctacaaac cagcaacatg aaatggacaa accaatctgc ttaagatcct | 1380 |
| gtcatagttt tagatcattg gttatcctga tttgcaaagt gatcaaaagc attctagcca | 1440 |
| tgtgcaacca acaccacca aaaataaaat caaacaaaac taagttgtga aggaagggag | 1500 |
| ggaaggtcat agccttctta agcagaggtg ttccattgtt ttagccaatc cttggttgaa | 1560 |
| tcttaggaat gaacagtgtc tcaagctcat tcacgtttca tgaccaactg gtagttggca | 1620 |
| ctgaaaaaac ttttcagggc tgtgtgaatt gtgtgactga ttgtcctaga tgcactactt | 1680 |
| tatttaaaaa ataatgttca taggagtca atatgtagtt taagagacaa tcagtgtgtg | 1740 |
| tcttataaat ggtacatctg tggttttttaa tctgtgctag acttcaaaac tgtgatctcc | 1800 |
| tgttattgta tgcaaccttg aactccacct ctgcaggggt tcttctgtga ttaaataggt | 1860 |
| tataattata agcaaaattc agagcaactg agtactgatc taaaaagatt acctttggct | 1920 |
| ggaggtgagc tgcactgaaa ctttacgaca aaatgtctct ggacaaagag agtcagagaa | 1980 |
| gagaagcaaa aggacactaa ttcatctgta atttactgtt ggtaagccta gcagtaaaga | 2040 |
| gacattggtc aattgctctg accctgatga attattaaac tgagatcatt gtcgtttatg | 2100 |
| cttgcagatg ttaaatggaa aagttatata tgcataaacc ttttcttcct ggatttggca | 2160 |
| gatatgtata attatattaa aatggttcta gcacaaaaaa aaaaaaaaa | 2209 |

<210> SEQ ID NO 3
<211> LENGTH: 289
<212> TYPE: PRT
<213> ORGANISM: Homo sapiens

<400> SEQUENCE: 3

```
Met Met Ser Tyr Leu Lys Gln Pro Pro Tyr Ala Val Asn Gly Leu Ser
 1               5                  10                  15
Leu Thr Thr Ser Gly Met Asp Leu Leu His Pro Ser Val Gly Tyr Pro
             20                  25                  30
Ala Thr Pro Arg Lys Gln Arg Arg Glu Arg Thr Thr Phe Thr Arg Ala
         35                  40                  45
Gln Leu Asp Val Leu Glu Ala Leu Phe Ala Lys Thr Arg Tyr Pro Asp
     50                  55                  60
Ile Phe Met Arg Glu Glu Val Ala Leu Lys Ile Asn Leu Pro Glu Ser
 65                  70                  75                  80
Arg Val Gln Val Trp Phe Lys Asn Arg Arg Ala Lys Cys Arg Gln Gln
                 85                  90                  95
Gln Gln Gln Gln Gln Asn Gly Gly Gln Asn Lys Val Arg Pro Ala Lys
                100                 105                 110
Lys Lys Thr Ser Pro Ala Arg Glu Val Ser Ser Glu Ser Gly Thr Ser
             115                 120                 125
Gly Gln Phe Thr Pro Pro Ser Ser Thr Ser Val Pro Thr Ile Ala Ser
         130                 135                 140
Ser Ser Ala Pro Val Ser Ile Trp Ser Pro Ala Ser Ile Ser Pro Leu
145                 150                 155                 160
Ser Asp Pro Leu Ser Thr Ser Ser Ser Cys Met Gln Arg Ser Tyr Pro
                 165                 170                 175
Met Thr Tyr Thr Gln Ala Ser Gly Tyr Ser Gln Gly Tyr Ala Gly Ser
             180                 185                 190
Thr Ser Tyr Phe Gly Gly Met Asp Cys Gly Ser Tyr Leu Thr Pro Met
         195                 200                 205
His His Gln Leu Pro Gly Pro Gly Ala Thr Leu Ser Pro Met Gly Thr
     210                 215                 220
Asn Ala Val Thr Ser His Leu Asn Gln Ser Pro Ala Ser Leu Ser Thr
225                 230                 235                 240
Gln Gly Tyr Gly Ala Ser Ser Leu Gly Phe Asn Ser Thr Thr Asp Cys
                 245                 250                 255
Leu Asp Tyr Lys Asp Gln Thr Ala Ser Trp Lys Leu Asn Phe Asn Ala
             260                 265                 270
Asp Cys Leu Asp Tyr Lys Asp Gln Thr Ser Ser Trp Lys Phe Gln Val
         275                 280                 285
Leu
```

<210> SEQ ID NO 4
<211> LENGTH: 2082
<212> TYPE: DNA
<213> ORGANISM: Homo sapiens

<400> SEQUENCE: 4

| | | | | | |
|---|---|---|---|---|---|
| cctccgaagc | agtaaaccag | cccctctgtt | tgtttgtttg | ctttgccctt | agttccactg | 60 |
| ctccaaaccc | acccaccaag | gactctgaac | ctgtccaccc | cgggcgcatc | aagatcttcc | 120 |
| agctgggtac | ccccgatttg | gccgactttg | cacctccaa | acaaccttag | catgatgtct | 180 |
| tatcttaagc | aaccgcctta | cgcagtcaat | gggctgagtc | tgaccacttc | gggtatggac | 240 |
| ttgctgcacc | cctccgtggg | ctacccggcc | acccccggga | acagcgccg | ggagaggacg | 300 |
| acgttcactc | gggcgcagct | agatgtgctg | gaagcactgt | ttgccaagac | ccggtaccca | 360 |
| gacatcttca | tgcgagagga | ggtggcactg | aaaatcaact | tgcccgagtc | gagggtgcag | 420 |

-continued

```
gtatggttta agaatcgaag agctaagtgc cgccaacaac agcaacaaca gcagaatgga    480
ggtcaaaaca aagtgagacc tgccaaaaag aagacatctc cagctcggga agtgagttca    540
gagagtggaa caagtggcca attcactccc ccctctagca cctcagtccc gaccattgcc    600
agcagcagtg ctcctgtgtc tatctggagc ccagcttcca tctccccact gtcagatccc    660
ttgtccacct cctcttcctg catgcagagg tcctatccca tgacctatac tcaggcttca    720
ggttatagtc aaggatatgc tggctcaact tcctactttg ggggcatgga ctgtggatca    780
tatttgaccc ctatgcatca ccagcttccc ggaccagggg ccacactcag tcccatgggt    840
accaatgcag tcaccagcca tctcaatcag tccccagctt ctctttccac ccagggatat    900
ggagcttcaa gcttgggttt taactcaacc actgattgct tggattataa ggaccaaact    960
gcctcctgga agcttaactt caatgctgac tgcttggatt ataaagatca gacatcctcg   1020
tggaaattcc aggttttgtg aagacctgta gaacctcttt ttgtgggtga ttttaaata   1080
tactgggctg gacattccag ttttagccag gcattggtta aaagagttag atgggatgat   1140
gctcagactc atctgatcaa agttccgaga ggcatagaag gaaaaacgaa gggccttaga   1200
ggggcctaca aaccagcaac atgaaatgga caaaccaatc tgcttaagat cctgtcatag   1260
ttttagatca ttggttatcc tgatttgcaa agtgatcaaa agcattctag ccatgtgcaa   1320
ccaaacacca ccaaaaataa aatcaaacaa aactaagttg tgaaggaagg gagggaaggt   1380
catagccttc ttaagcagag gtgttccatt gtttagcca atccttggtt gaatcttagg   1440
aatgaacagt gtctcaagct cattcacgtt tcatgaccaa ctggtagttg gcactgaaaa   1500
aacttttcag ggctgtgtga attgtgtgac tgattgtcct agatgcacta ctttatttaa   1560
aaaataatgt tcataaggag tcaatatgta gtttaagaga caatcagtgt gtgtcttata   1620
aatggtacat ctgtggtttt taatctgtgc tagacttcaa aactgtgatc tcctgttatt   1680
gtatgcaacc ttgaactcca cctctgcagg ggttcttctg tgattaaata ggttataatt   1740
ataagcaaaa ttcagagcaa ctgagtactg atctaaaaag attacctttg gctggaggtg   1800
agctgcactg aaactttacg acaaaatgtc tctggacaaa gagagtcaga gaagagaagc   1860
aaaaggacac taattcatct gtaatttact gttggtaagc ctagcagtaa agagacattg   1920
gtcaattgct ctgaccctga tgaattatta aactgagatc attgtcgttt atgcttgcag   1980
atgttaaatg gaaagttat atatgcataa acctttctt cctggatttg gcagatatgt   2040
ataattatat taaatggtt ctagcacaaa aaaaaaaaa aa                        2082
```

<210> SEQ ID NO 5
<211> LENGTH: 289
<212> TYPE: PRT
<213> ORGANISM: Mus musculus

<400> SEQUENCE: 5

Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
            20                  25                  30

Ala Thr Pro Arg Lys Gln Arg Arg Glu Arg Thr Thr Phe Thr Arg Ala
        35                  40                  45

Gln Leu Asp Val Leu Glu Ala Leu Phe Ala Lys Thr Arg Tyr Pro Asp
    50                  55                  60

Ile Phe Met Arg Glu Glu Val Ala Leu Lys Ile Asn Leu Pro Glu Ser
65                  70                  75                  80

```
Arg Val Gln Val Trp Phe Lys Asn Arg Arg Ala Lys Cys Arg Gln Gln
                85                  90                  95
Gln Gln Gln Gln Gln Asn Gly Gly Gln Asn Lys Val Arg Pro Ala Lys
            100                 105                 110
Lys Lys Ser Ser Pro Ala Arg Glu Val Ser Ser Glu Ser Gly Thr Ser
        115                 120                 125
Gly Gln Phe Ser Pro Pro Ser Ser Thr Ser Val Pro Thr Ile Ala Ser
    130                 135                 140
Ser Ser Ala Pro Val Ser Ile Trp Ser Pro Ala Ser Ile Ser Pro Leu
145                 150                 155                 160
Ser Asp Pro Leu Ser Thr Ser Ser Ser Cys Met Gln Arg Ser Tyr Pro
                165                 170                 175
Met Thr Tyr Thr Gln Ala Ser Gly Tyr Ser Gln Gly Tyr Ala Gly Ser
            180                 185                 190
Thr Ser Tyr Phe Gly Gly Met Asp Cys Gly Ser Tyr Leu Thr Pro Met
        195                 200                 205
His His Gln Leu Pro Gly Pro Gly Ala Thr Leu Ser Pro Met Gly Thr
    210                 215                 220
Asn Ala Val Thr Ser His Leu Asn Gln Ser Pro Ala Ser Leu Ser Thr
225                 230                 235                 240
Gln Gly Tyr Gly Ala Ser Ser Leu Gly Phe Asn Ser Thr Thr Asp Cys
                245                 250                 255
Leu Asp Tyr Lys Asp Gln Thr Ala Ser Trp Lys Leu Asn Phe Asn Ala
            260                 265                 270
Asp Cys Leu Asp Tyr Lys Asp Gln Thr Ser Ser Trp Lys Phe Gln Val
        275                 280                 285
Leu

<210> SEQ ID NO 6
<211> LENGTH: 1737
<212> TYPE: DNA
<213> ORGANISM: Mus musculus

<400> SEQUENCE: 6
caggtttatc tggtctcact ccatcccctc tagttttgga gctgctgggg ggtgggggg         60
acggcggggg tggggacgc atctgcaact cctttaaaag cctgtgccca gcgtctcccg       120
ggttcttttt agttagtgct ggaacgtgga ggaagctgct ccctccgaag cagtaaacca       180
gcatttctgt ttgtttgttt gctttgcccct tagttccgtc actccaaatc tacccaccaa      240
ggaccctgac cctgtccact ccaggcgaat cgagaccgtc cggctgggtc ccccaatt        300
gggccgactt tgcgcctcca acaaccttta gcatgatgtc ttatctaaag caaccgcctt       360
acgcagtcaa tgggctgagt ctgaccactt cgggtatgga cttgctgcat ccctccgtgg       420
gctaccccgc acccccccgg aaacagcgaa gggagaggac gacatttact agggcacagc      480
tcgacgttct ggaagctctg tttgccaaga cccggtaccc agacatcttc atgagggaag      540
aggtggcact gaaaatcaac ttgccagaat ccagggtgca ggtatggttt aagaatcgaa      600
gagctaagtg ccgccaacag cagcagcagc agcagaatgg aggtcagaac aaagtgaggc      660
ctgccaagaa gaagagctct ccagctcggg aagtgagttc agagtgga acaagtggcc       720
agttcagtcc ccctctagt acctcagtcc caaccattgc cagcagcagt gctccagtgt      780
ctatctggag cccagcgtcc atctccccac tgtctgaccc cttgtccact tcctcctcct      840
gcatgcagag gtcctatccc atgacctata ctcaggcttc aggttatagt caaggctatg      900
```

```
ctggctcaac ttcctacttt gggggcatgg actgtggatc ttatttgacc cctatgcatc      960
accagcttcc tggaccaggg gccacactca gtcccatggg taccaatgct gttaccagcc     1020
atctcaatca gtccccagct tctctttcca cccagggata tggagcttca agcttgggtt     1080
ttaactcaac cactgattgc ttggattata aggaccaaac tgcctcttgg aagcttaact     1140
tcaatgctga ctgcttggat tataaagatc agacgtcctc atggaaattc caggttttgt     1200
gaagacctgt agaagctatt tttgtgggtg atttttaaat atgctgggct gaacattcca     1260
gttttagcca ggcattggtt aaaaaagtta gatggaacga tgctctcaga ctcctgatca     1320
aagttaccga gaggcataga aggaaaaagg aagggccctt agaagggtcc atcaaccagc     1380
aacctgaaat ggacaaacca atctacttaa gattctgtta tagttctaga tcattggttt     1440
cctgatttgc aaatgattga tcaaatatat tctagcgaca tgcaaccaaa taccactcaa     1500
aacaaaaatc cagcaaaact gagttgtgag ggaagggagg gaaggtcatg gccttcaaag     1560
cagaggtgat ccggtgtttt agccaatctt tggttgaatc ttaggaatgg acaatgtccc     1620
aggctcattc acgtttcatg accaacaggt agttggcact gaaaaacttt tcagggctgt     1680
gtggattgtg cgactgattg tcctagatgc actactttat ttaaaaaaaa aaaaaaa        1737
```

REGENERATION AND NEOGENESIS OF RETINAL VISUAL CELL-EXPRESSING OTX2 PROTEIN

This application is a U.S. national stage of International Application No. PCT/JP2004/001023 filed Feb. 2, 2004.

TECHNICAL FIELD

The present invention relates to an agent for inducing differentiation into retinal photoreceptor cells, an agent for preventing/treating/suppressing progression of retinal diseases, and a diagnostic agent for retinal diseases, which contain an Otx2 protein or a gene encoding an Otx2 protein.

BACKGROUND ART

Retinal photoreceptor cells are only one photosensor in a mammal, and has previously been intensively studied physiologically, biochemically, anatomically and clinically (JP-A-2002-325571). However, mechanism of development and differentiation into retinal photoreceptor cells has been unknown at all. As a causative locus for human genetic retinal degeneration which is a disease resulting from abnormalities of retinal photoreceptor cells, at least 145 loci are known, but an established method of treating the disease has not been present yet, and patients are suffering from severe eyesight disorder. Therefore, elucidation of causes, and establishment of therapeutic method for retinal degeneration leading to loss of eyesight or severe eyesight disorder have been desired. In addition, since degeneration or dyscrasia of retinal photoreceptor cells is seen in many retinal diseases such as not only retinitis pigmentosa, but also diabetic retinopathy and macular degeneration, it is very important to elucidate molecular mechanism of development and differentiation of retinal photoreceptor cells, in order to enable degeneration or neogenesis of retinal photoreceptor cells,

DISCLOSURE OF THE INVENTION

An object of the present invention is to provide an agent for preventing, treating or suppressing progression of retinal diseases including retinal degeneration. Another object of the present invention is to provide a method for screening a compound useful as medicines. A further object of the present invention is to provide an agent of, or a method of diagnosing retinal diseases. A still further object of the present invention is to provide a method for inducing differentiation, or an agent for inducing differentiation into retinal photoreceptor cells which are suitable for transplantation in the retina of patients suffering from retinal diseases.

The present inventors have paid their attention to an Otx2 protein belonging to the same gene family as that of a transcription factor Crx which has previously been analyzed as a key of differentiation into retinal photoreceptor cells, and analyzed the role of an Otx2 protein in determining the fate of a retinal photoreceptor cell. As a result of analysis at a level of a mouse living body, the present inventors have found that an Otx2 protein is very important in determining the fate of a retinal photoreceptor cell. That is, when an Otx2 gene was incorporated into a virus vector to infect a mouse undifferentiated retinal stem cell with the recombinant vector, and to express an Otx2 protein in a mouse undifferentiated retinal stem cell, most of undifferentiated retinal stem cells were differentiated into retinal photoreceptor cells. Based on such finding, the present inventors have further studied to complete the present invention.

That is, the present invention relates to:

(1) an agent for preventing, treating or suppressing progression of a retinal disease, which comprises an Otx2 protein or its partial peptide, or a salt thereof, (2) the agent according to the above (1), wherein the Otx2 protein is a protein comprising the same amino acid sequence as, or substantially the same amino acid sequence as an amino acid sequence represented by SEQ ID NO: 1, SEQ ID NO: 3 or SEQ ID NO: 5,(3)

(3) an agent for preventing, treating or suppressing progression of a retinal disease, which comprises a DNA or an RNA encoding an Otx2 protein or its partial peptide, (4) the agent according to the above (3), wherein the DNA comprises a nucleotide sequence represented by SEQ ID NO: 2, SEQ ID NO: 4 or SEQ ID NO: 6, or a nucleotide sequence which hybridizes with the said sequence under highly stringent conditions, (5) the agent according to the above (3), which comprises a recombinant vector containing a DNA or an RNA encoding an Otx2 protein or its partial peptide, (6) an agent for inducing differentiation into a retinal photoreceptor cell, which comprises an Otx2 protein or its partial peptide, or a salt thereof, (7) an agent for inducing differentiation into a retinal photoreceptor cell, which comprises a DNA or an RNA encoding an Otx2 protein or its partial peptide, (8) a method for inducing differentiation into a retinal photoreceptor cell, which comprises expressing an Otx2 protein, or increasing an amount of expression of an Otx2 protein, (9) the method for inducing differentiation into a retinal photoreceptor cell according to the above (8), which comprises expressing an Otx2 protein, or increasing an amount of expression of an Otx2protein in an eye ball tissue-derived cell, an embryonic stem cell, a neural stem cell or a neural precursor cell,

(10) the method for inducing differentiation into a retinal photoreceptor cell according to the above (8), wherein a DNA or an RNA encoding an Otx2 protein or its partial peptide is introduced into an eye ball tissue-derived cell, an embryonic stem cell, a neural stem cell or a neural precursor cell, and the resulting cell is cultured,

(11) a method for preventing, treating or suppressing progression of a retinal disease, which comprises administering an effective amount of Otx2 protein or its partial peptide, or a salt thereof to a mammal,

(12) a method for preventing, treating or suppressing progression of a retinal disease, which comprises administering an effective amount of a DNA or an RNA encoding an Otx2 protein or its partial peptide to a mammal,

(13) a method for regenerating retina, which comprises transplanting a retinal photoreceptor cell or a precursor cell thereof which is differentiation-induced by an Otx2 protein, into retina,

(14) use of an Otx2 protein or its partial peptide, or a salt thereof for preparing an agent for preventing, treating or suppressing progression of a retinal disease,

(15) use of a DNA or an RNA encoding an Otx2 protein or its partial peptide for preparing an agent for preventing, treating or suppressing progression of a retinal disease.

(16) a diagnostic agent for a retinal disease, which comprises an antibody to an Otx2 protein or its partial peptide, or a salt thereof,

(17) a method for diagnosing a retinal disease, which comprises using an antibody to an Otx2 protein or its partial peptide, or a salt thereof,

(18) a method for diagnosing a retinal disease, which comprises detecting an expression amount or a mutation of an Otx2 protein or its partial peptide,

(19) a diagnostic agent for a retinal disease, which comprises (a) a DNA or an RNA encoding an Otx2 protein or a partial peptide, or (b) an antisense polynucleotide comprising a nucleotide sequence complementary or substantially complementary to a nucleotide sequence of the said DNA or RNA,

(20) a method for diagnosing a retinal disease, which comprises using (a) a DNA or an RNA encoding an Otx2 protein or its partial peptide, or (b) an antisense polynucleotide comprising a nucleotide sequence complementary or substantially complementary to a nucleotide sequence of the said DNA or RNA,

(21) a method for screening a compound having an action of inducing differentiation into a retinal photoreceptor cell, or a salt thereof, which comprises using, as an index, an expression of, or increase in an expression amount of an Otx2 protein or its partial peptide,

(22) the screening method according to the above (21), wherein a cell having an ability of expressing an Otx2 protein or its partial peptide is used,

(23) a kit for screening a compound having an action of inducing differentiation into a retinal photoreceptor cell, or a salt thereof, which comprises a cell having an ability of expressing an Otx2 protein or its partial peptide,

(24) a compound having an action of inducing differentiation into a retinal photoreceptor cell, or a salt thereof, which is obtainable using a screening method as defined in the above (21) or (22), or a screening kit as defined in the above (23), and

(25) a medicine, which comprises a compound as defined in the above (24) or a salt thereof.

Using the protein of the present invention or the DNA of the present invention, an eye ball tissue-derived cell, an embryonic stem cell, a neural stem cell or a neural precursor cell can be differentiated into a retinal photoreceptor cell. Therefore, by regenerating or newly producing a retinal photoreceptor cell using the protein of the present invention or the DNA of the present invention, retinal diseases such as retinitis pigmentosa, senile macular degeneration, diabetic retinopathy, retinal detachment, glaucoma and retinal vessel occlusion can be prevented or treated, or progression of such disease can be suppressed. Further, since retinal photoreceptor cells undergo structural or functional abnormalities due to abnormality of an Otx2 gene, diagnosis of such retinal diseases can be performed by detecting abnormality of an Otx2 gene, or degeneration or reduction in expression of an Otx2 protein.

BEST MODE FOR CARRYING OUT THE INVENTION

Figure 1:
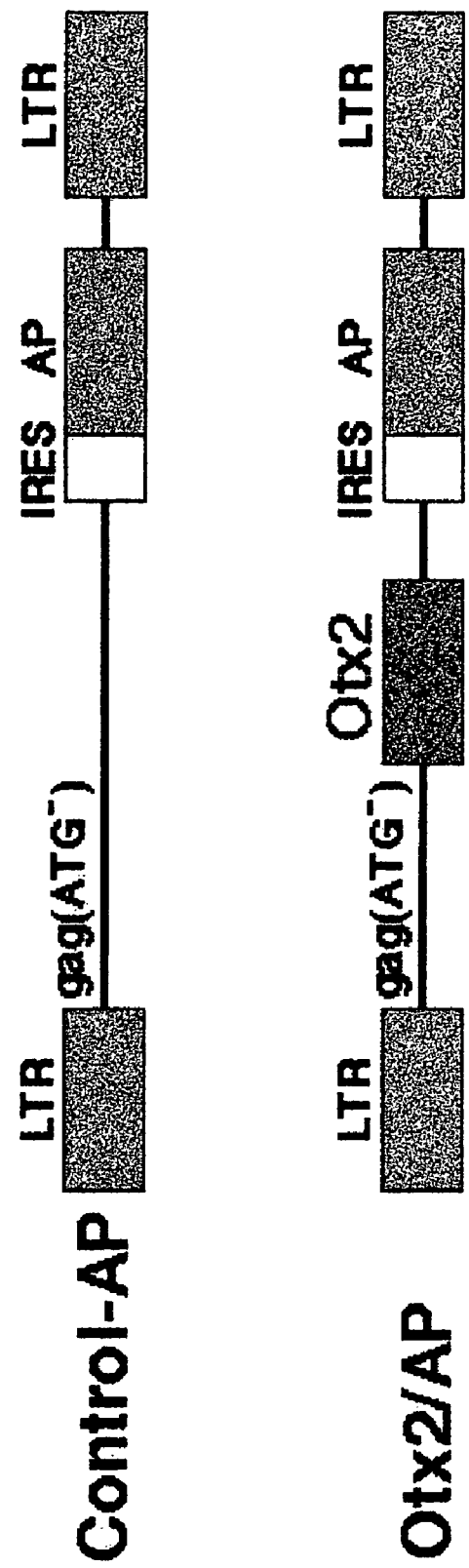
FIG. 1 is a view showing the structure of a control virus vector and an Otx2 virus vector. In the figure, AP represents a placenta-derived alkaline phosphatase gene, and LTR represents a virus promoter. When Otx2 virus vector has IRES sequence between Otx2 and AP, the vector allows for coexpression of both genes (Otx2 and AP). The IRES sequence is a virus-derived gene.

Examples of Otx2 proteins used in the present invention include a protein containing the same or substantially the same amino acid sequence as an amino acid sequence represented by SEQ ID NO: 1, 3 or 5. In the present invention, the Otx2 proteins are not limited to a human-derived Otx2 protein having an amino acid sequence represented by SEQ ID NO: 1 or 3, and a mouse-derived Otx2 protein having an amino acid sequence represented by SEQ ID NO: 5, but may have an amino acid sequence derived from other animals, particularly, a warm-blooded animal (e.g. guinea pig, mouse, chicken, rabbit, pig, sheep, cow, monkey, etc.), or substantially the same amino acid sequence as the said sequence.

Examples of the "amino acid sequence substantially the same as an amino acid sequence represented by SEQ ID NO: 1, 3 or 5" include amino acid sequences having not less than about 50%, preferably not less than about 60%, more preferably not less than about 70%, further preferably not less than about 80%, inter alia, preferably not less than about 90%, most preferably not less than about 95% homology with an amino acid sequence represented by SEQ ID NO: 1, 3 or 5. As a protein containing an amino acid sequence which is substantially the same as an amino acid sequence represented by SEQ ID NO: 1, 3 or 5 of the present invention, for example, a protein containing an amino acid sequence which is substantially the same as an amino acid sequence represented by SEQ ID NO: 1, 3 or 5, and having an action of inducing differentiation into a retinal photoreceptor cell is preferable. Inter alia, it is preferable that transcription activity, and action of inducing differentiation into a retinal photoreceptor cell are equivalent to a protein having an amino acid sequence represented by SEQ ID NO: 1, 3 or 5 (e.g. about 0.01 to 100 fold, preferably about 0.5 to 20 fold, more preferably about 0.5 to 2 fold), and extent of such activity or quantitative elements such as molecular weight of proteins may differ. Measurement of action of inducing differentiation into a retinal photoreceptor cell can be performed according to the known method, for example, such action can be measured according to a screening method described later. Measurement of transcription activity can be performed using the known method such as reporter assay and RT-PCR.

Specifically, as an Otx2 protein used in the present invention, there is used a protein containing (a) an amino acid sequence in which one or two or more (preferably, around 1 to 30, more preferably around 1 to 40, still more preferably several (1 to 5)) of amino acids in an amino acid sequence represented by SEQ ID NO: 1, 3 or 5 are deleted, (b) an amino acid sequence in which one or two or more (preferably, around 1 to 30, more preferably around 1 to 10, still more preferably several (1 to 5)) of amino acids are added to an amino acid sequence represented by SEQ ID NO: 1, 3 or 5, (c) an amino acid sequence in which one or two or more (preferably, around 1 to 30, more preferably around 1 to 10, still more preferably several (1 to 5)) of amino acids in an amino acid sequence represented by SEQ ID NO: 1, 3 or 5 are substituted with other amino acids, or (d) an amino acid sequence as a combination thereof. The amino acid which is added in the (b), and the amino acid which is substituted in the (c) may be a non-natural amino acid other than 20 kinds of amino acids encoded by a gene. It is more preferable that the protein described in the (a) to (d) has an action of inducing differentiation into a retinal photoreceptor cell.

In the Otx2 proteins of the present invention, the C-terminus may be any one of carboxyl group (—COOH), carboxylate (—COO$^-$), amide (—CONH$_2$) and ester (—COOR). Herein, as R in the ester group, there are used a $C_{1-6}$ alkyl group such as methyl, ethyl, n-propyl, isopropyl and n-butyl; a $C_{3-8}$ cycloalkyl group such as cyclopentyl and cyclohexyl; a $C_{6-12}$ aryl group such as phenyl and α-naphthyl; and a $C_{7-14}$ aralkyl group such as a phenyl-$C_{1-2}$ alkyl group (e.g. benzyl and phenethyl) and an α-naphthyl-$C_{1-2}$ alkyl group (e.g. α-naphthylmethyl); and additionally, a pivaloyloxymethyl group which is generally used as an oral ester. When the Otx2 protein in the present invention has a carboxyl group (or carboxylate) at a position other than the C-terminus, the protein in which a carboxyl group is amidated or esterified is also included in the Otx2 protein of the present invention. In this case, as the ester, for example, the aforementioned C-terminal ester is used. Further, the Otx2 protein in the present invention includes a protein in which the amino group of N-terminal methionine residue is protected with a protecting group (e.g. $C_{1-6}$ acyl group such as $C_{2-6}$ alkanoyl group including, for example, formyl and acetyl), a protein in which a glutamyl group produced by cleavage at the N-terminal in a living body is converted into pyroglutamic acid, a protein in which a substitutable group (e.g. —OH, —SH, amino group, imidazole group, indole group, guanidine group, etc.) on a side chain of an amino acid in the molecule is protected with an appropriate protecting group (e.g. $C_{1-6}$ acyl group such as $C_{2-6}$ alkanoyl group including, for example, formyl group and acetyl), and a so-called conjugated protein such as glycoprotein to which a sugar chain is bound.

As a partial peptide of Otx2 proteins used in the present invention (hereinafter, abbreviated as partial peptide in some cases), any one may be used as far as it is a partial peptide of the Otx2 protein. As the number of amino acids of such partial peptide in the present invention, a peptide containing an amino acid sequence of at least about not less than 20, preferably about not less than 50, or more preferably about not less than 100 amino acids among a constitutional amino acid sequence of the Otx2 protein is preferable.

In a partial peptide of the present invention, the C-terminus may be any one of carboxyl group (—COOH), carboxylate (—COO$^-$), amide (—CONH$_2$) and ester (—COOR). Further, the partial peptide of the present invention includes, like the Otx2 protein of the present invention, a partial peptide wherein the amino group of methionine residue at the N-terminus is protected with a protecting group, a partial peptide wherein Gln produced by cleavage of the N-terminal side in a living body is converted into pyroglutamic acid, a partial peptide wherein a substituent on the side chain of an amino acid in the molecule is protected with an appropriate protecting group, and a conjugated peptide such as a so-called glycopeptide to which a sugar chain is bound.

Examples of a salt of the Otx2 protein of the present invention or a partial peptide thereof include physiologically acceptable salts with an acid or a base. Inter alia, physiologically acceptable acid addition salts are preferable. Examples of such salts include salts with inorganic acids (e.g. hydrochloric acid, phosphoric acid, hydrobromic acid, sulfuric acid), or with organic acids (e.g. acetic acid, formic acid, propionic acid, fumaric acid, maleic acid, succinic acid, tartaric acid, citric acid, malic acid, oxalic acid, benzoic acid, methansulfonic acid, benzene sulfonic acid).

The Otx2 protein in the present invention or a salt thereof can be prepared from a cell or a tissue of an animal, preferably a warm-blooded animal, more preferably human or rat, further preferably human, particularly preferably human brain neuron, ocular retinal pigment epithelial cell or a retinal photoreceptor cell by the known method of purifying a protein, or can also be prepared by culturing a transformant containing a DNA or an RNA encoding the Otx2 protein of the present invention described later. Alternatively, such protein can also be prepared in the same or similar manner to a protein synthesis method described later. When the protein is prepared from animal tissues or cells, animal tissues or cells are homogenized, extracted with an acid, and the extract can be purified and isolated by combining chromatographies such as reverse phase chromatography, and ion exchange chromatography.

For synthesizing an Otx2 protein in the present invention or a partial peptide thereof or a salt thereof or an amide thereof, a commercially available protein synthesis resin can be usually used. Examples of such resin include a chloromethyl resin, a hydroxymethyl resin, a benzhydrylamine resin, an aminomethyl resin, a 4-benzyloxybenzyl alcohol resin, a 4-methylbenzhydrylamine resin, a PAM resin, a 4-hydroxymethyl methylphenylacetamido methyl resin, a polyacrylamide resin, a 4-(2',4'-dimethoxyphenyl-hydroxymethyl)phenoxy resin, and a 4-(2',4'-dimethoxyphenyl-Fmoc-aminoethyl)phenoxy resin. Using such resin, amino acids in which an α-amino group, and a side chain functional group are appropriately protected are condensed in the order of the sequence of desired proteins on a resin by the known various condensing methods. At the end of the reaction, the protein is cleaved from the resin, and at the same time, various protecting groups are removed, and further, an intramolecular disulfide bond forming reaction is performed in a highly diluted solution, thereby to obtain a desired protein or an amide thereof. Regarding the aforementioned condensation of protected amino acids, various activating reagents which can be used in synthesizing proteins can be used. As an activating reagent, carbodiimides are particularly preferable. As the carbodiimides used, there are exemplified DCC, N,N'-diisopropylcarbodiimide, N-ethyl-N'-(3-dimethylaminoprolyl)carbodiimide. In the activation by these reagents, the protected amino acid may be added to a resin after activation of a protected amino acid is performed in advance by adding a protected amino acid directly to a resin together with a racemization suppressing additive (e.g. HOBt, HOOBt), or by converting a protected amino acid into symmetric acid anhydride or HOBt ester or HOOBt ester.

A solvent used in activation of a protected amino acid or condensation with a resin can be appropriately selected from solvents which are known to be usable in a protein condensing reaction. Such solvents include, for example, acid amides such as N,N-dimethylformamide, N,N-dimethylacetamide, and N-methylpyrrolidone; halogenated hydrocarbons such as methylene chloride, and chloroform; alcohols such as trifluoroethanol; sulfoxides such as dimethyl sulfoxide; ethers such as pyridine, dioxane and tetrahydrofuran; nitriles such as acetonitrile, and propionitrile; esters such as methyl acetate and ethyl acetate, and an appropriate mixture thereof. The reaction temperature is appropriately selected from a range which is known to be usable in a protein bond formation, and is usually appropriately selected from a range of −20° C. to 50° C. An activated amino acid derivative is usually used in 1.5 to 4-fold excessive amount. When condensation is found to be insufficient as a result of a test using a ninhydrine reaction, it is possible to perform sufficient condensation by repeating a condensing reaction without removal of protecting groups. When sufficient condensation is not resulted even after repeated reactions, unreacted amino acids may be acetylated using acetic anhydride or acetylimidazole.

Examples of protecting groups used for an amino group of a raw material include, for example, Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, and Fmoc. A carboxyl group can be protected, for example, by alkyl esterification (e.g. linear, branched, or cyclic alkyl esterification such as methyl, ethyl, propyl, butyl, t-butyl, cyclopentyl, cyclohexyl, cycloheptyl, cyclooctyl, and 2-adamantyl esters), aralkyl esterification (e.g. benzyl ester, 4-nitrobenzyl ester, 4-methoxybenzyl ester, 4-chlorobenzyl ester, benzhydryl ester), phenacyl esterification, benzyloxycarbonyl hydrazide formation, t-butoxycarbonyl hydrazide formation, or trityl hydrazide formation. The hydroxy group of serine can be protected, for example, by esterification or etherification. As a group suitable for this esterification, for example, a lower alkanoyl group such as an acetyl group, an aroyl group such as a benzoyl group, and a group derived from carbonic acid such as a benzyloxycarbonyl group and an ethoxycarbonyl group are used. In addition, a group suitable for etherification is, for example, a benzyl group, a tetrahydropyranyl group, or a t-butyl group. As a protecting group for the phenolic hydroxy group of tyrosine, for example, Bzl, $Cl_2$-Bzl, 2-nitrobenzyl, Br-Z, and t-butyl are used. As a protecting group for the imidazole of histidine, for example, Tos, 4-methoxy-2,3,6-trimethylbenzenesulfonyl, DNP, benzyloxymethyl, Bum, Boc, Trt and Fmoc are used.

As an activated carboxyl group of a raw material, for example, corresponding acid anhydride, azide, and active ester [ester with alcohol (e.g. pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt)] are used. As an activated amino group of a raw material, for example, corresponding phosphoric acid amide is used. As a method of removing (deprotecting) a protecting group, there are used, for example, (a) catalytic reduction in a hydrogen stream in the presence of a catalyst such as Pd-black or Pd-carbon, (b) acid treatment with anhydrous hydrogen fluoride, methanesulfonic acid, trifluoromethanesulfonic acid, trifluoroacetic acid or a mixed solution thereof, (c) base treatment with diisopropylethylamine, triethylamine, piperidine, or piperazine, or (d) reduction with sodium in liquid ammonia. The deprotection by the above-mentioned acid treatment is generally performed at a temperature of about −20° C. to 40° C., but in such acid treatment, it is effective to add a scavenger for cations, such as anisole, phenol, thioanisole, m-cresol, p-cresol, dimethyl sulfide, 1,4-butanedithiol, and 1,2-ethanedithiol. The 2,4-Dinitrophenyl group used as a protecting group for the imidazole of histidine is removed by thiophenol treatment. The formyl group used as a protecting group for the indole of tryptophan may also be removed by alkali treatment with dilute sodium hydroxide solution, dilute ammonia or the like, in addition to deprotection by acid treatment in the presence of 1,2-ethanedithiol or 1,4-butanedithiol.

Protection of functional groups which should not be involved in the reaction of raw materials, and protecting groups therefor, and deprotection of such protecting groups, and activation of the functional groups involved in the reaction can be appropriately selected from the known groups or the known means. As an alternative method of obtaining protein amides, for example, an α-carboxyl group of carboxyl terminal amino acid is first protected by amidation, a peptide (protein) chain is extended at the amino group side to a desired chain length, a protein in which only a protecting group for an α-amino group at the N-terminus of the peptide chain is removed, and a protein in which only a protecting group for the carboxyl group at the C-terminus is removed are prepared, and both these proteins are condensed in the aforementioned mixed solvent. Details of the condensation reaction are the same as described above. After the protected protein obtained by condensation is purified, all protecting groups can be removed by the aforementioned method to obtain desired crude protein. This crude protein is purified by using various known purification means, and main fractions are lyophilized, thereby to give a desired protein amide. For obtaining an ester entity of proteins, an α-carboxyl group of carboxyl terminal amino acids is condensed with a desired alcohol to obtain an amino acid ester, and then a desired ester of proteins can be obtained similarly according to the procedure in the preparation of protein amides. When a protein obtained by the aforementioned method is a free compound, it can be converted into an appropriate salt by the known method, and conversely, when the protein is obtained as a salt, it can be converted into a free compound by the known method.

A partial peptide or a salt of the Otx2 protein in the present invention can be prepared according to the known peptide synthesis method, or by cleavage of the Otx2 protein in the present invention with an appropriate peptidase. As a method of synthesizing a peptide, for example, any one of a solid phase synthesis method and a liquid phase synthesis method may be used. That is, a desired peptide can be prepared by condensing a partial peptide or an amino acid which can constitute the Otx2 protein of the present invention, with a remaining part, and removing the protecting group when the product has a protecting group. Examples of the known condensing method and deprotection of protecting groups include methods described, for example, in the following (a) to (e): (a) M. Bodanszky and M. A. Ondetti, Peptide Synthesis, Interscience Publishers, New York (1966), (b) Schroeder and Luebke, The Peptide, Academic Press, New York (1965), (c) Nobuo Izumiya et al., Base and experiment of peptide synthesis, Maruzen (1975), (d) Haruaki Yajima and Shunpei Sakakibara, Biochemistry Experimental Course 1, Chemistry of Protein IV, 205, (1977), and (e) Development of Medicines, vol. 14, Sequel, Peptide Synthesis, supervised by Haruaki Yajima, Hirokawashoten.

In addition, after the reaction, the partial peptide of the present invention can be purified and isolated by a conventional purification method, for example, in combination of solvent extraction/distillation/column chromatography/liquid chromatography/recrystallization. When the partial peptide obtained by the aforementioned method is a free compound, it can be converted into an appropriate salt by the known method, and conversely, when it is obtained as a salt, it can be converted into a free compound by the known method.

As a DNA encoding an Otx2 protein used in the present invention, any one of a genomic DNA, a genome DNA library, a cDNA derived from the aforementioned cells/tissues, a cDNA library derived from the aforementioned cells/tissues, and a synthetic DNA may be used. A vector used in a library may be any one of bacteriophage, plasmid, cosmid, and phagemide. In addition, a DNA can also be amplified directly by Reverse Transcriptase Polymerase Chain Reaction (hereinafter, abbreviated as RT-PCR method) using a total RNA or mRNA fraction prepared from the aforementioned cells/tissues. Specifically, examples of a DNA encoding an Otx2 protein include (a) a DNA comprising a nucleotide sequence represented by SEQ ID NO: 2, 4 or 6, and (b) a DNA having a nucleotide sequence which hybridizes with a nucleotide sequence represented by SEQ ID NO: 2, 4 or 6 under highly stringent conditions, and encoding an Otx2 protein having substantially the same quality of activity (e.g. transcription activity, retinal photoreceptor cell differentiation inducing action, etc.) as that of the Otx2 protein of the present invention. SEQ ID NOS: 2 and 4 are a DNA encoding a human Otx2 protein (Kastury, K., et al., "Chromosome locations of human EMX and OTX genes", Genomics 22 (1), 41-45 (1994)), and SEQ ID NO: 6 is a DNA encoding a mouse Otx2 protein (Simeone, A., et al., "Nested expression domains of four homeobox genes in developing rostral brain", Nature 358 (6388), 687-690 (1992)). As a DNA which can hybridize with a nucleotide sequence represented by SEQ ID NO: 2, 4 or 6, for example, there is used a DNA comprising a nucleotide sequence having about not lower than 70% homology, preferably about not lower than 80% homology, more preferably about not lower than 90% homology, most preferably about not less than 95% homology, with a nucleotide sequence represented by SEQ ID NO: 2, 4 or 6. Hybridization can be performed according to the known method or a similar method thereof, for example, the method described in Molecular cloning $2^{nd}$ J. Sambrook et al., Cold Spring Harbor Lab. Press, 1989). In addition, when a commercially available library is used, hybridization can be performed according to the method described in the instruction manual attached thereto. More preferably, such hybridization can be performed according to highly stringent conditions. The highly stringent conditions indicate, for example, conditions of a sodium concentration of about 19 to 40 mM, preferably about 19 to 20 mM, and a temperature of about 50 to 70° C., preferably about 60 to 65° C. In particular, most preferable conditions are that the sodium concentration is about 19 mM and the temperature is about 65° C.

As a DNA encoding a partial peptide used in the present invention, any DNA comprising a nucleotide sequence encoding the aforementioned partial peptide of the present invention may be used. Alternatively, any one of a genomic DNA, a genome DNA library, a cDNA derived from the aforementioned cells/tissues, a cDNA library derived from the aforementioned cells/tissues, and a synthetic DNA may be used. A vector used in a library may be any one of bacteriophage, plasmid, cosmid, and phageimide. In addition, a DNA may be amplified directly by Reverse Transcriptase Polymerase Chain Reaction (hereinafter, abbreviated as RT-PCR method) using an mRNA fraction prepared from the aforementioned cells/tissues. Specifically, as a DNA encoding a partial peptide of the present invention, for example, such DNA to be used includes, for example, (a) a DNA containing a partial nucleotide sequence of a DNA comprising a nucleotide sequence represented by SEQ ID NO: 2, 4 or 6, (b) a DNA containing a nucleotide sequence which hybridizes with a DNA comprising a nucleotide sequence represented by SEQ ID NO: 2, 4 or 6 under highly stringent conditions, and encoding a protein having substantially the same quality of activity (e.g. transcription activity, retinal photoreceptor cell differentiation inducing action, etc. ) as that of the Otx2 protein of the present invention, and a DNA containing a partial nucleotide sequence of the (a) or (b).

Although an RNA encoding an Otx2 protein or its partial peptide used in the present invention is not particularly limited as far as it can express an Otx2 protein or its partial peptide by a transcriptase, it can be obtained by the known means.

As a means for cloning a DNA completely encoding an Otx2 protein in the present invention or a partial peptide thereof (hereinafter, abbreviated as present protein in some cases), the DNA can be amplified by using a synthetic DNA primer containing a partial nucleotide sequence of a protein of the present invention by a PCR method, or can be selected from a DNA incorporated into an appropriate vector, by hybridization using a DNA fragment or a synthetic DNA encoding a part or an entire region of the labeled present protein. A method of hybridization can be performed according to the method described, for example, in Molecular Cloning $2^{nd}$ J. Sambrook et al., Cold Spring Harbor Lab. Press, 1989. In addition, when a commercially available library is used, hybridization can be performed according to the method described in the instruction manual attached thereto.

Substitution of a nucleotide sequence of a DNA can be performed using PCR or the known kit, for example, Mutan™-superExpress Km (TAKARA SHUZO CO., LTD.), or Mutan™-K (TAKARA SHUZO CO., LTD.) by the known method such as the ODA-LAPCR method, the gapped duplex method, and the Kunkel method, or a similar method thereof. The cloned DNA encoding a protein of the present invention can be used as it is, depending on the purpose, or can be used, if desired, by digesting with a restriction enzyme or by adding a linker. The DNA has ATG as a translation initiation codon at the 5'-end, and has TAA, TGA or TAG as a translation termination codon at the 3'-end. These translation initiation codon and translation termination codon may be added using an appropriate synthetic DNA adaptor.

A DNA or an RNA encoding the protein of the present invention (hereinafter, abbreviated as present DNA, in some cases) may be modified based on the following strategy, i.e. to more stabilize the present DNA in a cell, to enhance the cell permeability of the present DNA, and to reduce the toxicity of the present DNA, if any. Many modifications like these are known in the art, and are disclosed, for example, in J. Kawakami et al, Pharm Tech Japan, Vol. 8, pp. 247, 1992; Vol. 8. pp. 395, 1992; S. T. Crooke et al. ed., Antisense Research and Applications, CRC Press, 1993. The present DNA may be used in a special form in which the DNA is encapsulated in a liposome or a microsphere. In addition, other substances other than a base may be added to the present DNA. Examples of other substances include a sugar; an acid or a base; a polycation compound such as polylysine acting to neutralize a charge of a phosphate nucleus; and a hydrophobic substance such as lipid (e.g. phospholipid, cholesterol, etc.) which enables to enhance interaction with a cell membrane, or to increase uptake of nucleic acids. Examples of preferable lipids to be added include cholesterol and a derivative thereof (e.g. cholesteryl chloroformate, cholic acid, etc.). Other substance described above can be attached to the 3'-end or 5'-end of nucleic acids, and can be attached via a base, a sugar, or an intramolecular nucleoside bond. The present DNA may be chemically modified at the terminus. Examples of groups for such terminal modification include a group for cap specifically arranged at 3'-end or 5'-end of nucleic acids, which suppress degradation due to nuclease such as exonuclease, and RNase. Examples of such groups for cap include a hydroxy-protecting group known in the art, including glycols such as polyethylene glycol and tetraethylene glycol, though they are not limited thereto.

As a recombinant vector containing a DNA or RNA encoding the Otx2 protein or its partial peptide used in the present invention, an expression vector capable of expressing an Otx2 protein or its partial peptide is preferable.

An expression vector of the protein of the present invention can be prepared by (i) excising a DNA fragment containing a DNA encoding the present protein from, for example, cDNA and (ii) ligating said DNA fragment in the downstream direction of a promoter in an appropriate expression vector.

As the above expression vector, there are used *Escherichia coli*-derived plasmid (e.g. pCR4, pCR2.1, pBR322, pBR325, pUC12, pUC13), *Bacillus subtilis*-derived plasmid (e.g. pUB110, pTP5, pC194), yeast-derived plasmid (e.g. pSH19, pSH15), bacteriophage such as λ phage, virus such as retrovirus, adenovirus, lentivirus, vaccinia virus, and baculovirus and, additionally, pA1-11, pXT1, pRc/CMV, pRc/RSV, and pcDNAI/Neo. Inter alia, as a vector used in the present invention, a virus is preferable, and retrovirus, adenovirus and lentivirus are more preferable.

As the promoter described above, any promoter may be used as far as it is an appropriate promoter corresponding to a host used in the expression of the gene. For example, when an animal cell is used as a host, examples of such promoters include SRα promoter, SV40 promoter LTR promoter, CMV promoter, and HSV-TK promoter. Among them, it is preferable to use LTR promoter, CMV promoter, or SRα promoter. When a host is a bacterium of the genus *Escherichia*, trp promoter, lac promoter, recA promoter, $\lambda P_L$ promoter, and lpp promoter are preferable. When a host is a bacterium of the genus *Bacillus*, SPO1 promoter, SPO2 promoter, and penP promoter are preferable. When a host is yeast, PHO5 promoter, PGK promoter, GAP promoter, and ADH promoter are preferable. When a host is an insect cell, polyhedrin promoter, and P10 promoter are preferable.

As an expression vector, expression vectors containing optionally, in addition to the above elements, an enhancer, a splicing signal, a poly A addition signal, a cap structure, a protein synthesis initiation signal, a selectable marker, a labeled marker, and SV40 replication origin can be used.

Examples of the selectable marker include dihydrofolate reductase (hereinafter, abbreviated as dhfr in some cases) gene [methotrexate (MTX) resistance], ampicillin resistant gene (hereinafter, abbreviated as $Amp^r$ in some cases), and neomycin resistant gene (hereinafter, abbreviated as $Neo^r$ in some cases, G418 resistance). In particular, when a dhfr gene is employed as a selectable marker using dhfr gene-deficient Chinese hamster cell CHO, an objective gene may be selected on a medium containing no thymidine.

As the labeled marker, an alkaline phosphatase (hereinafter, abbreviated as AP in some cases) gene, and green fluorescent protein (GFP) gene can be preferably used.

In addition, a signal sequence suitable for a host may be optionally added to an expression vector. When a host is a bacterium of the genus *Escherichia*, PhoA signal sequence, and OmpA signal sequence can be utilized. When a host is a bacterium of the genus *Bacillus*, α-amylase signal sequence, and subtilisin signal sequence can be utilized. When a host is yeast, MFα signal sequence, and SUC2 signal sequence can be utilized. When a host is an animal cell, insulin signal sequence, α-interferon signal sequence, and antibody molecule signal sequence can be utilized.

When a virus is used as a vector, in order to enhance translation mechanism, it is preferable to arrange an IRES (interior ribosome-binding site) sequence as a protein synthesis initiation signal.

By introducing into a host the thus constructed expression vector containing a DNA encoding the protein of the present invention, a transformant can be prepared.

As a host, for example, *Escherichia* bacteria, *Bacillus* bacteria, yeasts, insect cells, insects, and animal cells are used. As an embodiment of *Escherichia* bacteria, there are used *Escherichia coli* K12/DH1 (Proc. Natl. Aced. Sci. USA, vol. 60, 160 (1968)), JM103 (Nucleic acids Research, vol. 9, 309 (1981)), JA221 (Journal of Molecular Biology vol. 120, 517 (1978)), HB101 (Journal of Molecular Biology, vol. 41, 459 (1969)), C600 (Genetics, vol. 39, 440 (1954)), DH5α (Inoue, H., Nojima, H. and Okayama, H., Gene, 96, 23-28 (1990)), and DH10B (Proc. Natl. Acad. Sci. USA, vol. 87, 4645-4649 (1990)). As *Bacillus* bacteria, for example, *Bacillus subtilis* MI114 (Gene, vol. 24, 255 (1983)), and 207-21 (Journal of Biochemistry, vol. 95, 87 (1984)) are used. As yeast, for example, *Saccharomyces cerevisiae* AH22, $AH22R^-$, NA87-11A, DKD-5D, 20B-12, *Schizosaccharomyces pombe* NCYC1913, NCYC2036, and *Pichia pastoris*.

As an insect cell, for example, when a virus is AcNPV, there are used cabbage armyworm larva-derived established cell (*Spodoptera frugiperda* cell; Sf cell), MG1 cell derived from *Trichoplusia ni* midgut, High Five™ cell derived from *Trichoplusia ni* egg, *Mamestrabrassicae*-derived cell and *Estigmena acrea*-derived cell. When a virus is BmNPV, silkworm-derived established cell (*Bombyx mori* N; BmN cell) is used. As the said Sf cell, for example, Sf9 cell (ATCC CRL1711), and Sf21 cell (Vaughn, J. L. et al, In Vivo, 13, 213-217, (1977)) are used. As an insect, for example, silkworm larva is used (Maeda et al., Nature, vol. 315, 592 (1985)). As an animal cell, for example, monkey cell (COS-7, Vero, Chinese Hamster cell CHO (hereinafter, abbreviated as CHO cell), dhfr gene-deficient Chinese Hamster cell CHO (hereinafter, abbreviated as CHO (dhfr) cell), mouse L cell, mouse AtT-20, mouse myeloma cell, rat GH3 , and human FL cell are used.

In order to transform *Escherichia* bacteria, transformation can be preformed according to the method described, for example, in Proc. Natl. Acad. Sci. USA, vol. 69, 2110 (1972) or Gene, vol. 17, 107 (1982). In order to transform *Bacillus* bacteria, transformation can be performed according to the method described, for example, in Molecular & General Genetics, vol. 168, 111 (1979). In order to transform yeast, transformation can be preformed according to the method described, for example, in Methods in Enzymology, vol. 194, 182-187 (1991), Proc. Natl. Acad. Sci. USA, vol. 75, 1929 (1978). In order to transform insect cells or insects, transformation can be performed according to the method described, for example, in Bio/Technology, vol. 6, 47-55 (1988). In order to transform animal cells, transformation can be preformed according to the method described, for example, in Cell Technology separate volume 8 New Cell Technology Experimental Protocol, 263-267 (1995) (published by Shujunsha), Virology, vol. 52, 456 (1973). Like this, a transformant transformed with an expression vector containing a DNA encoding a protein of the present invention is obtained. When a transformant of which host is *Escherichia* bacterium or *Bacillus* bacterium is cultured, a liquid medium is suitable for a culture medium, and a carbon source, a nitrogen source, an inorganic substance and other additives which are required to grow a transformant are contained therein. Examples of the carbon source include glucose, dextrin, soluble starch, and sucrose, examples of the nitrogen source include inorganic or organic substances such as ammonium salts, nitrate salts, corn steep liquor, peptone, casein, meat extract, soybean meal, and potato extract, and examples of inorganic substances include calcium chloride, sodium dihydrogen phosphate, and magnesium chloride. In addition, yeast extract, vitamins, and growth promoting factor may be added. Medium pH is desirably about 5 to 8.

As a medium upon culturing of *Escherichia* bacteria, for example, M9 medium containing glucose and casamino acid (Miller, Journal of Experiments in Molecular Genetics, 431-433, Cold Spring Harbor Laboratory, New York, 1972) is preferable. Herein, in order to make a promoter act effectively, for example, a drug such as 3β-indolylacrylic acid may be added, if required. When a host is *Escherichia* bacterium, culturing is performed usually at about 15° C. to 43° C. for about 3 to 24 hours, and if necessary, aeration or stirring may be carried out. When a host is *Bacillus* bacterium, culturing is usually performed at about 30 to 40° C. for 6 to 24 hours, and if necessary, aeration or stirring may be performed. When a transformant of which host is yeast is cultured, examples of a medium include Burkholder minimum medium (Bostian, K. L. et al, Proc. Natl. Acad. Sci. USA, vol. 77, 4505 (1980)), and a SD medium containing 0.5% casamino acid (Bitter, G. A. et al., Proc. Natl. Acad. Sci. USA, vol. 81, 5330 (1984)). It is preferable to adjust the pH of the medium to about 5 to 8. Culturing is usually performed at 20° C. to 35° C. for about 24 to 72 hours, and if necessary, aeration or stirring may be optionally performed.

When a transformant of which host is an insect cell or an insect is cultured, there is used, as a medium, a medium in which an additive such as immobilized 10% bovine serum is appropriately added to Grace's Insect Medium (Grace T. C. C., Nature, vol. 195, 788 (1962)). It is preferable to adjust the pH of the medium to about 6.2 to 6.4. Culturing is performed usually at about 27° C. for about 3 to 5 days, and if necessary, aeration or stirring may be optionally performed. When a transformant of which host is an animal cell is cultured, there are used as a medium, for example, MEM medium containing about 5 to 20% fetal bovine serum (Science, vol. 122, 501 (1952)), DMEM medium (Virology, vol. 8, 396 (1959)), RPMI 1640 medium (The Journal of the American Medical Association, vol. 199, 519 (1967)), and 199 medium (Proceeding of the Society for the Biological Medicine, vol. 73, 1 (1950)) are used. It is preferable that the pH is about 6 to 8. Culturing is usually performed at 30° C. to 40° C. for about 15 to 60 hours, and if necessary, aeration or stirring may be performed. As described above, the protein of the present invention can be produced in a cell, in a cell membrane or outside a cell of a transformant.

In order to separate and purify the protein of the preset invention from the culture broth, for example, separation and purification can be performed by the following method. When the protein of the present invention is extracted from cultured bacterial cells or cells, there are appropriately employed a method of colleting bacterial cells or cells by the known method after culturing, suspending these cells in an appropriate buffer, disrupting the suspended cells by ultrasound, lysozyme and/or freezing/melting, and obtaining the crude extract of the protein by centrifugation or filtration, and the like. A protein degenerating agent such as urea and guanidine hydrochloride, or a surfactant such as Triton X-100™ may be contained in a buffer. When a protein is secreted in a culture solution, after completion of the culturing, bacterial cells or cells and the culture supernatant are separated by the known method, and the culture supernatant is collected. Purification of a protein contained in the resulting extract or the culture supernatant can be performed by appropriate combination with the known separation/purification methods. As the known separation or purification method, there are used a method of utilizing solubility such as salting out and solvent precipitation method; a method of utilizing mainly differences in a molecular weight of a dialysis method, an ultrafiltration method, a gel filtration method, and an SDS-polyacrylamide gel electrophoresis method; a method of utilizing differences in charge such as ion exchange chromatography; a method of utilizing specific affinity such as affinity chromatography; a method of utilizing differences in hydrophobicity such as reverse phase high performance liquid chromatography; a method of utilizing differences in an isoelectric point such as isoelectric point electrophoresis method.

When the thus obtained protein is produced as a free form, it can be converted into a salt by the known method or a similar method, and conversely, when the protein is obtained as a salt, it can be converted into a free form or other salt by the known method or a similar method. By acting an appropriate protein modifying enzyme on a protein produced by a trasnformant before purification and after purification, arbitrary modification may be performed, or a polypeptide may be partially removed. As a protein modifying enzyme, there are used trypsin, chymotrypsin, arginyl endopeptidase, protein kinase, and glycosidase.

By expressing an Otx2 protein, or by increasing an expression amount of an Otx2 protein, differentiation into a retinal photoreceptor cell can be induced. Specifically, for example, in an eye ball tissue-derived cell, an embryonic stem cell, a neural stem cell or a neural precursor cell, the aforementioned cells can be differentiation-induced into a retinal photoreceptor cell by expressing an Otx2 protein, or by increasing an expression amount of an Otx2 protein. For this reason, (a) an Otx2 protein or its partial peptide, or a salt thereof, or (b) a DNA or an RNA encoding an Otx2 protein or its partial peptide can be used as an agent for inducing differentiation into a retinal photoreceptor cell.

The "inducing differentiation into a retinal photoreceptor cell" may occur in vivo or ex vivo. That is, an agent for inducing differentiation into a retinal photoreceptor cell of the present invention may be administered to a living body to induce in vivo differentiation into a retinal photoreceptor cell. Alternatively, an agent for inducing differentiation into a retinal photoreceptor cell of the present invention can be applied ex vivo to, for example, an eye ball tissue-derived cell, an embryonic stem cell, a neural stem cell or a neural precursor cell, and the aforementioned cells may be differentiation-induced into a retinal photoreceptor cell. More specifically, a DNA of the present invention is introduced into an eye ball tissue-derived cell, an embryonic stem cell, a neural stem cell, a neural precursor cell, and the resulting cell is cultured, thereby to induce differentiation of the cell into a retinal photoreceptor cell. Upon introduction of the present DNA, other gene may be introduced jointly. Examples of other gene include a retinal specific homeobox gene. Examples of a retinal-specific homeobox gene include a gene which has a specific expression pattern in eye region, and regulates the region specific pattern formation, and a gene involved in expression of differentiated character in a development process. Specific examples include Crx, Chx10, Pax6, and Rax.

Preferable examples of the "eye ball tissue" include an inner layer tissue of the optic cup. Such tissue may be derived from an adult, or may be derived from an individual at an embryonic stage. Examples of the "eye ball tissue-derived cell" include a fetal neural retina, a corpus ciliare cell such as a corpus ciliare pigment epithelial cell or a retinal pigment epithelial cell, a corpus ciliare epithelial cell, and an iris cell.

The eye ball tissue-derived cell can be collected, for example, by treating a tissue isolated by an appropriate means with Dispase or EDTA, treating subsequently the tissue with trypsin to separate into a single cell, further culturing cells in an appropriate medium to confluent, and subjecting the obtained cell to trypsin and collagenase treatment. Herein, when culturing is performed for the collection of cells, it is possible to use media such as a medium containing basic fibroblast growth factor, a medium containing epithelial cell growth factor, and a medium containing ILF (leukocyte migration inhibitory factor) can be used. Examples of the medium containing basic fibroblast growth factor (bFGF) include a serum-free medium containing bFGF, more specifically, DMEM/F12 containing $N_2$ supplements. The content of the bFGF in such medium is not less than about 10 ng/ml, preferably not less than about 20 ng/ml, more preferably not less than about 40 ng/ml. Examples of $N_2$ supplements include about 5 μg/ml of insulin, about 100 μg/ml of transferrin, about 20 nM of progesterone, about 100 μM of culturing cells in an appropriate medium to confluent, and about 30 nM of sodium selenate. Culturing conditions such as temperature, oxygen concentration and carbon dioxide concentration can be appropriately set, depending on the cells.

A neural stem cell or a neural precursor cell may be derived from an eye ball tissue-derived cell, or an embryonic stem cell, or may be derived from other cell or tissue. Specific examples include a fetal retina-derived neural stem cell, an adult corpus ciliare-derived retinal stem cell, an iris-derived retinal stem cell, a brain-derived neural stem cell, a retinal precursor cell, and an iris-derived neural precursor cell.

A method of inducing a neural stem cell or a neural precursor cell from an eye ball tissue-derived cell or an embryonic stem cell or other cell or tissue may be performed according to the known method. For example, examples of a method of inducing a neural stem cell or a neural precursor cell from an embryonic stem cell include the procedure described, for example, in the reference of Kawasaki, Sasai et al. (Kawasaki, H., Sasai Y., Neuron., 2000 October; 28(1):31-40). Regarding conditions for culturing and maintenance of an embryonic stem cell, for example, "Molecular Biology Protocol" (published by Nankodo) can be referenced. The neural stem cell or the neural precursor cell is obtained as a neural sphere containing this in some cases, but in the present invention, such neural sphere may be subjected to the following procedure.

A method of introducing the DNA of the present invention and optional other gene into an eye ball tissue-derived cell, an embryonic stem cell, a neural stem cell or a neural precursor cell, preferably, the neural stem cell or the neural precursor cell is not particularly limited, but the known method may be used, and examples of such method include a method for introducing a gene with the use of an adenovirus vector, a method for introducing a gene with the use of a retrovirus vector, a method for introducing a gene with the use of an adeno-associated virus, lipofection and electroporation. From a viewpoint of an introduction efficiency, preferably, a method for introducing a gene with the use of an adenovirus vector and a method for introducing a gene with the use of a retrovirus vector are desirable.

A cell with a gene introduced therein is cultured under differentiation inducing conditions suitable for differentiation into a retinal photoreceptor cell. Since differentiation inducing condition is different depending on a kind of a cell with a gene introduced therein, the condition can not be set primarily and can be appropriately selected. For example, examples of the differentiation inducing conditions include culturing in the presence of retinoic acid and serum. Herein, examples of a medium which can be used in culturing include the aforementioned DMEM/F12 medium containing $N_2$ supplements. It is desirable that an amount of the retinoic acid to be used is not less than about 0.1 μM, preferably not less than about 0.5 μM, and not more than about 10 μM, preferably not more than about 5 μM. In addition, it is desirable that an amount of the serum to be used is about 1% at differentiation inducement. Further, conditions such as temperature, oxygen concentration during culturing, and carbon dioxide concentration can be appropriately set depending on a cell with a gene introduced therein.

A retinal photoreceptor cell obtained by the aforementioned differentiation inducing method of the present invention can be applied as a transplantation cell for a patient with a retinal degenerative disease such as retinitis pigmentosa, senile macular degeneration, retinal detachment, glaucoma and retinal vessel occlusion. The transplantation cell may be not only a cell which has been completely differentiated into a retinal photoreceptor cell, but also a precursor cell before differentiation into a retinal photoreceptor cell.

An Otx2 protein or its partial peptide, or a salt thereof or a DNA or an RNA encoding an Otx2 protein or its partial peptide thereof can be used as a medicine such as an agent for preventing, treating or suppressing progression of retinal diseases. Examples of the "retinal diseases" include retinal vessel disorders and retinal inflammatory and degeneration lesions derived from systemic diseases such as diabetes, hypertension, arterial sclerosis, anemia, leukemia, systemic lupus erythematosus, and connective tissue diseases such as scleroderma; and inborn error of metabolism such as Tay-Sacks disease and Vogt-Spielmeyer disease, as well as local retinal diseases including retinal vessel disorders such as retinopathy of prematurity, retinal vein occlusion, retinal artery occlusion and retinal periphlebitis; retinal inflammation and degeneration derived from retinal detachment and trauma; age-related retinal degenerative diseases such as senile disciform macular degeneration; and congenital retinal degenerative disease. In particular, an agent for preventing, treating or suppressing progression of retinal diseases of the present invention can be particularly effectively used in congenital retinal degenerative disease, retinitis pigmentosa, macular degeneration, diabetic retinopathy, retinal detachment, glaucoma or retinal vessel occlusion.

When the protein of the present invention is used as an agent for preventing/treating/suppressing progression of the aforementioned retinal diseases, such protein can be formulated into a preparation by a conventional means. On the other hand, when the DNA of the present invention is used as an agent for preventing/treating/suppressing progression of the retinal diseases, such DNA of the present invention alone, or after the DNA is inserted into an appropriate vector such as a retrovirus vector, an adenovirus vector, a lentivirus vector and an adenovirus-associated virus vector, can be formulated into a preparation according to a conventional means. The present DNA can be administered as it is or together with an assistant for promoting uptake with a gene gun or a catheter such as a hydrogel catheter.

For example, the present protein or the present DNA can be orally administered as a tablet optionally coated with a sugar, a capsule, an elixir, or a microcapsule, or can be parenterally administered in the form of an injection such as a sterile solution or a suspension with water or other pharmaceutically acceptable liquid. The preparation of the present invention can be prepared, for example, by admixing the present protein or the present DNA with the physiologically acceptable known carrier, flavor, excipient, vehicle, antiseptic, stabilizer or binder.

Examples of the additive which can be admixed in a tablet or a capsule include binders such as gelatin, corn starch, tragacanth, and gum arabic; excipients such as crystalline cellulose; swelling agents such as corn starch, gelatin, and alginic acid; lubricants such as magnesium stearate; sweeteners such as sucrose, lactose and saccharin; flavors such as peppermint, akamono (Gaultheria adenothrix) oil, and cherry. In the case of a capsule, a liquid carrier such as an oil and fat can be further contained. A sterile composition for injection can be formulated according to the procedure as that of a conventional formulation such as dissolution or suspension formation of an active ingredient in an aqueous solution or an oily solution for injection. As an aqueous solution for injection, for example, an isotonic solution containing physiological saline, glucose and other auxiliary agent (e.g. D-sorbitol, D-mannitol, sodium chloride, etc.) are used, and an appropriate solubilizer such as an alcohol (e.g. ethanol), a polyalcohol (e.g. propylene glycol, polyethylene glycol), and a nonionic surfactant (e.g. polysorbate 80 (trade mark), HCO-50) may be used together. As an oily solution, for example, a sesame oil and a soybean oil are used, and benzyl benzoate, and benzyl alcohol which are a solubilizer may be used together. Further, the sterile composition may contain, for example, a buffer (e.g. phosphate buffer, sodium acetate buffer), a soothing agent (e.g. benzalkonium chloride, procaine hydrochloride), a stabilizer (e.g. human serum albumin, polyethylene glycol), a preservative (e.g. benzyl alcohol, phenol), and an antioxidant. The sterile composition prepared is usually filled into an appropriate ample, and is provided as an injection Since the thus obtained preparation is safe and low toxic, it can be administered, for example, to a mammal (e.g. human, rat, mouse, rabbit, sheep, pig, cow, cat, dog, monkey, etc.). Since a dose of the present protein or the present DNA varies depending on administration subjects, subject organs, symptoms, and administration routes, it can not be said generally, but in the case of parenteral administration, the dose is about 0.01 to 10 mg/kg, preferably about 0.05 to 5 mg/kg, per day.

It is preferable that the agent for preventing/treating/suppressing progression of retinal diseases of the present invention is topically administered to eyes. Examples of a dosage form of such preparation for topical administration to eyes include eye drops, opthalmic ointments, powders, granules, tablets, capsules, and injections. In particular, it is suitable that the dosage form is in the form of eye drops (e.g. aqueous eye drops, aqueous suspension of eye drops, non-aqueous eye drops, or non-aqueous suspension of eye drops), ophthalmic ointments and injections. Such preparations can be prepared according to the conventional manner.

Examples of diluents for aqueous solutions or suspensions used in the preparation of eye drops include distilled water and physiological saline. In addition, examples of diluents for non-aqueous solutions or suspensions are vegetable oil, liquid paraffin, mineral oil, propylene glycol, and p-octyldodecanol. Further, various additives such as buffers, isotonics, preservatives, thickeners, stabilizers, antioxidants, pH adjusting agents and chelating agents which are capable of being usually admixed in eye drops can be appropriately admixed in the eye drops of the present invention. Preparation of such eye drops is performed by aseptic procedure or by sterilization treatment at an appropriate stage.

The above buffer is added for the purpose of maintaining the pH constant, for example, at about 5.0 to 8.0. For example, a borate buffer, a citrate buffer, a tartarate buffer, a phosphate buffer, and an acetate buffer are used. These buffers are added for the purpose of adding the buffers, that is, they are added in such a range that the pH is maintained constant, for example, within the aforementioned range. The isotonic is added for the purpose of rendering isotonic with a tear, and examples of such isotonics include saccharides such as glucose, mannitol, and sorbitol; polyhydric alcohols such as glycerin, polyethylene glycol, and propylene glycol; and salts such as sodium chloride, and sodium citrate. These isotonics are added in such an amount that an osmotic pressure of eye drops becomes equivalent to that of a tear. Further, as the preservative, for example, benzalkonium chloride, parabens, and chlorobutanol are used. Examples of the above thickener include glycerin, carboxymethylcellulose and carboxyvinyl polymer. Examples of the above stabilizers include sodium sulfite, and propylene glycol, examples of the above antioxidant include ascorbic acid, sodium ascorbate, tocopherol, and sodium thiosulfate, examples of the above pH adjusting agent include hydrochloric acid, citric acid, phosphoric acid, acetic acid, tartaric acid, sodium hydroxide, potassium hydroxide, sodium carbonate and sodium bicarbonate, and examples of the above chelating agent include sodium edetate and sodium citrate. Further, the eye drops may be lyophilized into a form which is used by dissolution in distilled water for injection upon use.

Ophthalmic ointments can be prepared under sterile conditions by mixing an active ingredient into a normally used base for ophthalmic ointments, followed by formulation according to the conventional method. Examples of the base for ophthalmic ointments include vaseline, zelen 50, plastibase, and Macrogol, and, further, for the purpose of enhancing hydrophilicity, a surfactant may be added. In addition, regarding the ophthalmic ointments, the aforementioned additives such as preservatives may also be admixed, if necessary.

Further, a preparation for topical opthalmic administration may be formulated into a sustained-release preparation, a DDS (drug delivery) preparation, or an intraocular implant preparation using a release controlling substance which can control the release of an Otx2 protein or its partial peptide, or a DNA encoding each of them in the eyes. Examples of the release controlling substance include the known per se polymer, copolymer, or a mixture thereof which is synthesized by non-catalyst dehydration polycondensation from one or more kinds of α-hydroxycarboxylic acids (e.g. glycholic acid, lactic acid, hydroxybutyric acid, etc.), hydroxydicarboxylic acids (e.g. malic acid, etc.), and hydroxytricarboxylic acids (e.g. citric acid, etc.), as well as biodegradable polymer substances such as poly-α-cyanoacrylic acid ester, polyamino acid (e.g. poly-γ-benzyl-L-glutamic acid, etc.), and maleic anhydride-based copolymer (e.g. styrene-maleic acid copolymer, etc.).

It is not possible to generally suggest a dose and administration frequency of the preparation for topical ophthalmic administration of the present invention, because they vary depending on administration subjects, symptoms, dosage forms, and therapeutic periods. Usually, in the case of eye drops, a preparation containing 0.001 to 10.0 w/v %, preferably 0.01 to 1.0 w/v %, of the present protein or the present DNA can be administered to an adult several times a day, preferably 1 to 6 times a day, per eye, at a few drops, preferably 1 to 4 drops per application. In the case of an ophthalmic ointment, a preparation containing 0.001 to 10.0 w/w %, preferably 0.01 to 1.0 w/w % of the present protein or the present DNA can be applied to an adult several times, preferably 1 to 6 times per day.

In the present invention, diagnosis of retinal diseases can be performed by detecting an Otx2 protein or its partial peptide, or a salt thereof (hereinafter, abbreviated as present protein in some case) in a test solution, or measuring an amount thereof. For example, when reduction in a concentration of the present protein is detected, it can be diagnosed, for example, that there is a high possibility that a person is suffering from a retinal disease, or will be suffered from a retinal disease in the future. Since an antibody to an Otx2 protein or its partial peptide, or a salt thereof (hereinafter, abbreviated as present antibody in some cases) can specifically recognize the present protein, it can be used in the detection and quantitation of the present protein in a test solution. That is, the present antibody can be used as a diagnostic agent for retinal diseases. In the diagnostic agent, an antibody molecule itself may be used, or a F(ab')$_2$, Fab' or Fab fraction of an antibody molecule may also be used. Alternatively, the present protein in a test solution may be detected by tissue staining.

The present antibody may be a polyclonal antibody or a monoclonal antibody as far as it is an antibody capable of recognizing the present protein. The present antibody can be prepared by using the present protein as an antigen according to the known process for preparing an antibody or anti-serum.

One example of the process for preparing a monoclonal antibody to the present protein will be described below.

(i) First, preparation of a cell producing a monoclonal antibody will be described. The present protein itself or together with a carrier or a diluent is administered to a mammal at a site where an antibody can be produced. In order to enhance antibody producing ability upon administration, complete Freund adjuvant or incomplete Freund adjuvant may be administered. Administration is usually performed once every 2 to 6 weeks at a total of 2 to 10 times. Examples of a mammal to be used include monkey, rabbit, dog, guinea pig, mouse, rat, sheep and goat, and mouse or rat is preferably used. Upon preparation of a cell producing a monoclonal antibody, a hybridoma producing a monoclonal antibody can be prepared by selecting an individual for which an antibody titre is recognized from a warm-blooded animal, for example, a mouse immunized with an antigen, collecting the spleen or lymph node 2 to 5 days after final immunization, and fusing an antibody-producing cell contained therein with a myeloma cell. Measurement of an antibody titre in antibody serum can be performed, for example, by reacting a labeled protein described later with an anti-serum, and measuring the activity of a labeling agent bound to an antibody. Fusion procedure can be performed according to the known method, for example, the Kohler and Milstein method (Nature, vol. 256, p. 495 (1975)). Examples of a fusion promoter include polyethylene glycol (PEG) and Sendai virus. Preferably, PEG is used. Examples of a myeloma cell include NS-1, P3U1 and SP2/0, and among of them, P3U1 is preferably used. A preferable ratio of the number of antibody-producing cells (spleen cell) and that of myeloma cells used is about 1:1 to 20:1, and PEG (preferably, PEG 1000 to PEG 6000) is added at a concentration of about 10 to 80%, and incubation is carried out at about 20 to 40° C., preferably about 30 to 37° C. for about 1 to 10 minutes, thereby to prepare fused cells effectively.

For screening a hybridoma producing a monoclonal antibody, various methods can be used, including (a) a method of adding a hybridoma culture supernatant to a solid phase (e.g. microplate) onto which an antigen such as the present protein is adsorbed directly or together with a carrier, subsequently adding an anti-immunoglobulin antibody (when a cell used in the cell fusion is mouse, an anti-mouse immunoglobulin antibody is used) or Protein A labeled with a radioactive substance or an enzyme, and detecting a monoclonal antibody bound to the solid phase, and (b) a method of adding a hybridoma culture supernatant to a solid phase onto which an anti-immunoglobulin antibody or Protein A is adsorbed, adding the present protein labeled with a radioactive substance or an enzyme, and detecting a monoclonal antibody bound to the solid phase. Selection of a monoclonal antibody can be performed according to the known method or a similar method, and such selection can be performed usually on a medium for an animal cell to which HAT (hypoxanthine, aminopterin, thymidine) is added. As a medium for selection and culturing, any medium may be used as far as a hybridoma can be grown. For example, RPMI 1640 medium containing about 1 to 20%, preferably about 10 to 20% fetal bovine serum, GIT medium containing about 1 to 10% fetal bovine serum (manufactured by Wako Pure Chemical Industries Co., Ltd.) and a serum-free medium for hybridoma culturing (SFM-101, manufactured by Nissui Pharmaceutical Co., Ltd.) can be used. The culturing temperature is usually about 20 to 40° C., preferably about 37° C. The culturing time is usually about 5 days to 3 weeks, preferably about 1 week to 2 weeks. Culturing can be usually performed under 5% carbon dioxide. An antibody titre of a hybridoma culturing supernatant can be measured as in the measurement of an antibody titre in the above anti-serum.

(ii) Then, a monoclonal antibody is separated and purified. Separation and purification of a monoclonal antibody can be performed according to a method of separating and purifying immunoglobulin [e.g. a salting out method, an alcohol precipitation method, an isoelectric precipitation method, an electrophoresis method, an adsorbing and desorbing method with ion exchanger (e.g. DEAE), an ultracentrifugation method, a gel filtration method, and a specific purification method of collecting only an antibody with an antigen binding to a solid phase or an active adsorbing agent such as Protein A or Protein G, and releasing the binding to obtain an antibody] as in conventional separation and purification of a polyclonal antibody.

One example of a process for preparing a polyclonal antibody to the present protein (hereinafter, abbreviated as "Present polyclonal antibody" in some cases) will be described below.

The preset polyclonal antibody can be prepared according to the known method or a similar method thereof. For example, the antibody can be prepared by making a complex of an immunological antigen (present protein, etc.) and a carrier protein, immunizing a mammal as in the aforementioned process for preparing a monoclonal antibody, collecting an antibody containing composition against the present protein from the immunized animal, and separating and purifying an antibody. Regarding a complex of an immunological antigen with a carrier protein used for immunizing a mammal, the kind of a carrier protein, and the ratio of mixing a carrier and a hapten is not particularly limited as far as an antibody can be effectively produced against a hapten immunized by crosslinking with a carrier. For example, a method of coupling bovine serum albumin, bovine thyroglobulin, keyhole lympet hemocyanin at a weight ratio of about 0.1 to 20, preferably about 1 to 5 relative to a hapten is used. In addition, for coupling a hapten with a carrier, various condensing agents can be used, including glutaraldehyde, a carbodiimide, a maleimide active ester, and an active ester reagent containing a thiol group or a dithiopyridyl group are used. A condensation product from a hapten and a carrier itself or together with a carrier and a diluent is administered to a warm-blooded animal at a site where an antibody can be produced. In order to enhance antibody productivity upon administration, complete Freund adjuvant or incomplete Freund adjuvant may be administered. Administration can be usually performed once per about 2 to 6 weeks at a total of about 3 to 10 times. A polyclonal antibody can be collected from blood or ascites, preferably blood of a mammal immunized by the aforementioned method. A polyclonal antibody titre in an anti-serum can be measured as in the aforementioned measurement of an antibody titre in anti-serum. Separation and purification of a polyclonal antibody can be performed according to a similar method of separating and purifying immunoglobulin to the aforementioned separation and purification of a monoclonal antibody.

A method of quantitating the present protein using an antibody of the present invention is not particularly limited, but examples of such methods include a method of detecting an amount of an antibody, an antigen or an antibody-antigen complex corresponding to an amount of an antigen (amount of the present protein, etc.) in a test solution by a chemical or physical means, and calculating an amount of an antigen in a test solution based on a standard curve produced with the use of a standard solution containing the known amount of an antigen from a detected value. For example, nephrometry, a competition method, an immunometric method and a sandwich method are preferably used, but from a viewpoint of sensitivity and specificity, it is particularly preferable to use a sandwich method described later. A labeling agent used in a quantitation method using a labeling substance includes, for example, a radioactive isotope element, an enzyme, a fluorescent substance, and a light emitting substance. As the radioactive isotope element, for example ($^{125}$I), ($^{131}$I), ($^3$H) and ($^{14}$C) are used. As the enzyme, those which are stable and have large specific activity are preferable, and for example, β-galactosidase, β-glucosidase, alkaline phosphatase, peroxidase, and malate dehydrogenase are used. As the fluorescent substance, for example, fluorescamine, and fluorescein isothiocyanate are used. As the light emitting substance, luminol, luminol derivative, luciferin and lucigenin are used. Further, biotin-avidin system may be used for binding an antibody or an antigen with a labeling agent.

When an antigen or an antibody is insolubilized in the aforementioned quantitation method, physical adsorption may be used, or chemical binding which is usually used for insolubilizing/immobilizing a protein or an enzyme may be used. As a carrier, for example, insoluble polysaccharides such as agarose, dextran and cellulose; synthetic resins such as polystyrene, polyacrylamine and silicone; and glass are used. In a sandwich method, an amount of the present protein in a test solution can be quantitated by reacting the insolubilized present monoclonal antibody with a test solution (primary reaction), further reacting the labeled present monoclonal antibody (secondary reaction), and measuring the activity of a labeling agent on an insolubilized carrier. The primary reaction and the secondary reaction may be performed in a reverse order, or may be performed at the same time. The labeling agent and the method of insolubilization are the same as described above. In addition, in an immunological quantitation method by a sandwich method, an antibody used in a solid phase antibody or a labeling antibody is not necessarily one kind, and a mixture of two or more kinds of antibodies may be used for the purpose of improving measurement sensitivity. In a method of quantitating the present protein by a sandwich method, as the present monoclonal antibodies used in a primary reaction and a secondary reaction, it is preferable to use antibodies having different sites for binding with the present protein. That is, antibodies used in a primary reaction and a secondary reaction are such that, for example, when an antibody used in a secondary reaction recognizes a C-terminal part of the present protein, an antibody recognizing a part other than the C-terminal part, for example, an N-terminal part, used in a primary reaction, is preferably used.

The present monoclonal antibody can also be used in a quantitation method other than a sandwich method, such as a competition method, an immunometric method and nephrometry. In the competition method, an antigen and a labeled antigen in a test solution are reacted competitively to an antibody, an unreacted labeled antigen (F) and a labeled antigen (B) bound with an antibody are separated (B/F separation), a label amount of either B or F is measured, and an amount of an antigen in a test solution is quantitated. Specifically, examples of the present method include (a) a liquid phase method wherein a soluble antibody is used as an antibody, and B/F separation is performed using polyethylene glycol and a second antibody to the antibody, and (b) a solid phase method using a solid phased antibody as a first antibody, or using a soluble antibody as a first antibody, and a solid phased antibody as a second antibody. In the immunometric method, after an antigen in a test solution and a solid phased antigen are reacted competitively against a constant amount of a labeled antibody, the solid phase and the liquid phase are separated, or an antigen in a test solution and an excessive amount of a labeled antibody are reacted, then, a solid phased antigen is added to bind an unreacted labeled antibody to a solid phase, and the solid phase and the liquid phase are separated. Then, the amount of a labeled antibody in any of phases is measured to quantitate the amount of an antigen in a test solution. In addition, in nephrometry, an amount of an insoluble precipitate produced as a result of an antigen antibody reaction in a gel or in a solution is measured. When an amount of an antigen in a test solution is small, and only a small amount of precipitate is obtained, laser nephrometry utilizing laser light scattering is preferably used.

When these individual immunological quantitation methods are applied to the present invention, normal technical consideration of a person skilled in the art may be added to an operation method according to conventional conditions in each method. For details of these general technical means, review, and books can be referenced (e.g. see "Radioimmunoassay" edited by Hiroshi Irie (Kodansha, published in 1974); Separate Volume 'Radioimmunoassay" edited by Hiroshi Irie (Kodansha, published in 1979); "Enzyme Immunoassay" edited by Eiji Ishikawa et al. (Igakushoin, published in 1978); "Enzyme Immunoassay" edited by Eiji Ishikawa (second edition) (Igakushoin, published in 1982); "Enzyme immunoassay" edited by Eiji Ishikawa et al. (third edition) (Igakushoin, published in 1987); "Methods in ENZYMOLOGY", Vol. 70 (Immunochemical Techniques (Part A)); ibid Vol. 73 (Immunochemical Techniques (Part B)); ibid Vol. 74 (Immunochemical Techniques (Part C)); ibid Vol. 84 (Immunochemical Techniques (Part D: Selected Immunoassays); ibid Vol. 92 (Immunochemical Techniques (Part E: Monoclonal antibodies and General Immunoassay Methods)); ibid Vol. 121 (Immunochemical Techniques (Part I: Hybridoma Technology and Monoclonal Antibodies)) (all published by Academic Press).

The present antibody can also be used for preparing an antibody column used for purifying the present protein, detecting the present protein in each fraction at purification, or analyzing behavior of the present protein in a test cell.

Since the present DNA, or an antisense polynucleotide comprising a nucleotide sequence which is complementary or substantially complementary to a nucleotide sequence of the present DNA can be used as a probe, and thus can detect abnormality (gene abnormality) of a DNA or a mRNA encoding the present protein or its partial peptide in a living body, in particular, in a living body of a mammal (e.g. human, rat, mouse, rabbit, sheep, pig, cow, cat, dog, monkey, etc.), they are useful, for example, as an agent for genetic diagnosis of damages of the DNA or the mRNA, or mutation, or reduction in expression. The genetic diagnosis using the present DNA or antisense polynucleotide can be performed, for example, by the known Northern hybridization or PCR-SSCP method (Genomics, vol. 5 , p. 874-879 (1989), Proceedings of the National Academy of Sciences of the USA, vol. 86, p. 2766-2770 (1989)). For example, when reduction in expression of a mRNA encoding the present protein or its partial peptide is detected by Northern hybridization, it can be diagnosed that there is a high possibility that a subject is suffering from a retinal disease, or will be suffered from a retinal disease in the future.

It is enough that the "antisense polynucleotide" is a polynucleotide having a nucleotide sequence complementary to a nucleotide sequence of the present DNA in at least a part, and capable of hybridizing the present DNA. Therefore, antisense polynucleotide may be not only an entity comprising a nucleotide sequence complementary to a nucleotide sequence of the present DNA, but also an entity comprising a nucleotide sequence substantially complementary to a nucleotide sequence of the present DNA. Examples of the antisense polynucleotide include an entity comprising a nucleotide sequence which hybridizes with the present DNA under highly stringent conditions. Examples of the antisense polynucleotide include other type polynucleotides other than the aforementioned polynucleotides, such as a polydeoxynucleotide containing 2-deoxy-D-ribose, a polynucleotide containing D-ribose, and an entity containing N-glycoside of a purine or pyrimidine base; other polymers having a non-nucleotide skeleton (e.g. commercially available protein nucleic acid, and polymer of nucleic acid having specific synthetic sequence); and other polymers having a special bond (provided that the polymer contains a nucleotide having arrangement permitting pairing of bases or addition of bases found in a DNA or an RNA). These may be a double-stranded DNA, a single-stranded DNA, a double-stranded RNA, a single-stranded RNA, or a DNA/RNA hybrid, and may be a non-modified polynucleotide (or non-modified oligonucleotide), or a known modified polynucleotide (or modified oligonucleotide) to which a modification is added. Examples of a modified polynucleotide include a polynucleotide having a label known in the art, a polynucleotide with a cap, a methylated polynucleotide, a polynucleotide in which one or more natural nucleotides are substituted with analogs, an intramolecular nucleotide-modified polynucleotide, a polynucleotide having a non-charge bond (e.g. methylphosphonate, phosphotriester, phosphoramidate, carbamate, etc.), a polynucleotide with a bond having a charge or a sulfur-containing bond (e.g. phosphorothioate, phosphorodithioate), a polynucleotide having, as aside group, a protein (nuclease, nuclease inhibitor, toxin, antibody, signal peptide, poly-L-lysine) or a saccharide (e.g. monosaccharide), a polynucleotide having an intercalent compound (e.g. acridine, solarene, etc.), a polynucleotide containing a chelating compound (e.g. metal, radioactive metal, boron, oxidative metal, etc.), a polynucleotide containing an alkylating agent, and a polynucleotide having a modified bond (e.g. α-anomer type nucleic acid). Herein, "nucleoside", "nucleotide" and "nucleic acid" may contain not only a purine and pyrimidine base, but also other modified heterocyclic base. These modified entities may contain methylated purine and methylated pyrimidine, acylated purine and acylated pyrimidine or other heterocycles. A modified polynucleotide having a saccharide as a side chain group may be such that a sugar part of a side chain is further modified, for example, one or more hydroxyl groups of a saccharide are substituted with a halogen or an aliphatic group, or are converted into a functional group such as ether and amine.

That is, the antisense polynucleotide of the present invention is an RNA, a DNA, or a modified nucleic acid (RNA, DNA). Examples of the modified nucleic acid include a sulfur derivative and a thiophosphate derivative of nucleic acid, and nucleic acid which is resistant to degradation of polynucleotide amide or oligonucleoside amide, which is not limited thereto.

Using expression or a rise in an expression amount of an Otx2 protein or its partial peptide as an index, a compound having action of inducing differentiation into a retinal photoreceptor cell or a salt thereof can be screened. The screening can be performed, for example, using a cell having an ability to express an Otx2 protein or its partial peptide.

Specifically, examples of such screening include a method for screening a compound having an action of inducing differentiation into a retinal photoreceptor cell or a salt thereof, characterized in that a cell having an ability to express an Otx2 protein or its partial peptide is cultured in the presence of a test compound, and expression of an Otx2 protein or a partial peptide thereof is detected, or an expression amount of them is measured. Examples of the "cell having an ability to express an Otx2 protein or its partial peptide" include a transformant cell having the aforementioned present DNA. Alternatively, the cell may be a cell originally having an ability to express an Otx2 protein or its partial peptide not based on gene recombinant technique. An amount of expression of the present protein can be measured using the aforementioned method of quantitating the present protein by separating and purifying the present protein from a cultured cell by the aforementioned method.

In addition, other aspect of the present screening method includes a method for screening a compound having an action of inducing differentiation into a retinal photoreceptor cell or a slat thereof, characterized in that a cell having an ability to express an Otx2 protein or its partial peptide thereof is cultured in the presence of a test compound, and an amount of a mRNA encoding an Otx2 protein (hereinafter, abbreviated as Otx2 mRNA in some cases) is measured using a DNA encoding the present protein or a complementary DNA thereof or a partial DNA thereof. More specifically, there is provided a method for screening a compound having an action of inducing differentiation into a retinal photoreceptor cell or a salt thereof, characterized in that comparison was made between (a) an amount of expression of an Otx2 mRNA when a cell having an ability to express an Otx2 protein or its partial peptide is cultured, and (b) an amount of an Otx2m RNA when a cell having an ability to express an Otx2 protein or its partial peptide is cultured in the presence of a test compound.

In order to perform comparison of expression amounts of a mRNA by a hybridization method, such comparison can be performed according to the known method or a similar method thereof, for example, the method described in Molecular Cloning, $2^{nd}$, J. Sambrook et al., Cold Spring Harbor Lab. Press, 1989. Specifically, measurement of an amount of a mRNA encoding an Otx2 protein is performed by contacting a mRNA extracted from a cell according to the known method with a DNA encoding the present protein or a complementary DNA thereof or a partial DNA thereof, and measuring an amount of a mRNA bound to a DNA encoding the present protein or a complementary DNA thereof or a partial DNA thereof. An amount of an Otx2 mRNA bound to a DNA encoding the present protein or a complementary DNA thereof or a partial DNA thereof can be easily measured by labeling a DNA encoding the present protein or its complementary DNA or a partial DNA thereof with, for example, a radioactive isotope element or a pigment. As the radioactive isotope element, for example, $^{32}P$ and $^{3}H$ are used and, as a pigment, fluorescent pigments such as fluorescein, FAM (manufactured by PE Biosystems), JOE (manufactured by PE Biosystems), TAMRA (manufactured by PE Biosystems), ROX (manufactured by PE Biosystems), Cy5 (manufactured by Amershan) and Cy3 (manufactured by Amershan) are used. Alternatively, an amount of an Otx2m RNA can also be measured by converting a RNA extracted from a cell into a cDNA with a reverse transcriptase, and measuring an amount of a cDNA which has been amplified by PCR using, as a primer, a DNA encoding the present protein or its complementary DNA or a partial DNA thereof.

There is provided a method for screening a compound having an action of controlling activity of a promoter or an enhancer of a DNA encoding an Otx2 protein or a salt thereof, further a method for screening a compound having an action of inducing differentiation into a retinal photoreceptor cell or a salt thereof, characterized in that the known promoter or enhancer region of the DNA encoding an Otx2 protein is cloned from a genome DNA, a cell transformed with a recombinant DNA ligated upstream of an appropriate reporter gene cultured in the presence of a test compound, and expression of a reporter gene in place of expression of an Otx2 protein is detected. As a reporter gene, a staining marker gene such as lacZ (β-galactosidase gene) is used. By measuring an amount of a reporter gene product (e.g. mRNA, protein) using the known method, a test compound of increasing an amount of a reporter gene product can be selected as a compound having an action of promoting activity of a promoter or an enhancer of an Otx2 gene, that is, a compound having an activity of promoting expression of an Otx2 protein or its partial peptide.

Examples of a test compound in the aforementioned present screening method include a peptide, a protein, a non-peptidic compound, a synthetic compound, a fermentation product, a cell extract, a plant extract, and an animal tissue extract, and these compounds may be a novel compound, or the known compound.

In order to perform the aforementioned screening method, the present screening kit contains (a) a cell having an ability to express an Otx2 protein or its partial peptide, (b) a DNA encoding the present protein or a complementary DNA thereof or a partial DNA thereof, or (c) a cell transformed with a DNA in which a promoter or an enhancer of a DNA encoding an Otx2 protein is ligated to a reporter gene.

A compound obtained using the present screening method or screening kit, or a salt thereof is useful as a drug such as the aforementioned agent for preventing, treating or suppressing progression of a retinal disease, and an agent for inducing differentiation into a retinal photoreceptor cell. The compound or a salt thereof, an agent for preventing, treating or suppressing progression of a retinal disease containing it, or an agent for inducing differentiation into a retinal photoreceptor cell containing it can be performed as in the present protein or DNA.

EXAMPLES

As shown in FIG. 1, a mouse Otx2 cDNA was incorporated into a LIA vector which is a retrovirus vector. A human placenta-derived alkaline phosphatase gene is incorporated into a LIA vector (control virus vector), and a cell infected with a virus derived from this vector expresses alkaline phosphatase as a marker. A cell infected with a virus derived from a LIA vector with an Otx2 gene incorporated therein (Otx2 virus vector) expresses an Otx2 protein and, at the same time, coexpresses alkaline phosphatase as a marker.

Using a cultured cell (Phoenix cell line) for producing a retrovirus, a control virus vector and an Otx2 virus vector were prepared, respectively, the resulting viruses were concentrated by ultracentrifugation (swing rotor, 21,000 rpm 4° C. for 2 hours) to prepare a virus solution having an infection efficiency of $1 \times 10^7$ pfu (plaque forming unit)/ml, respectively.

Figure 2:
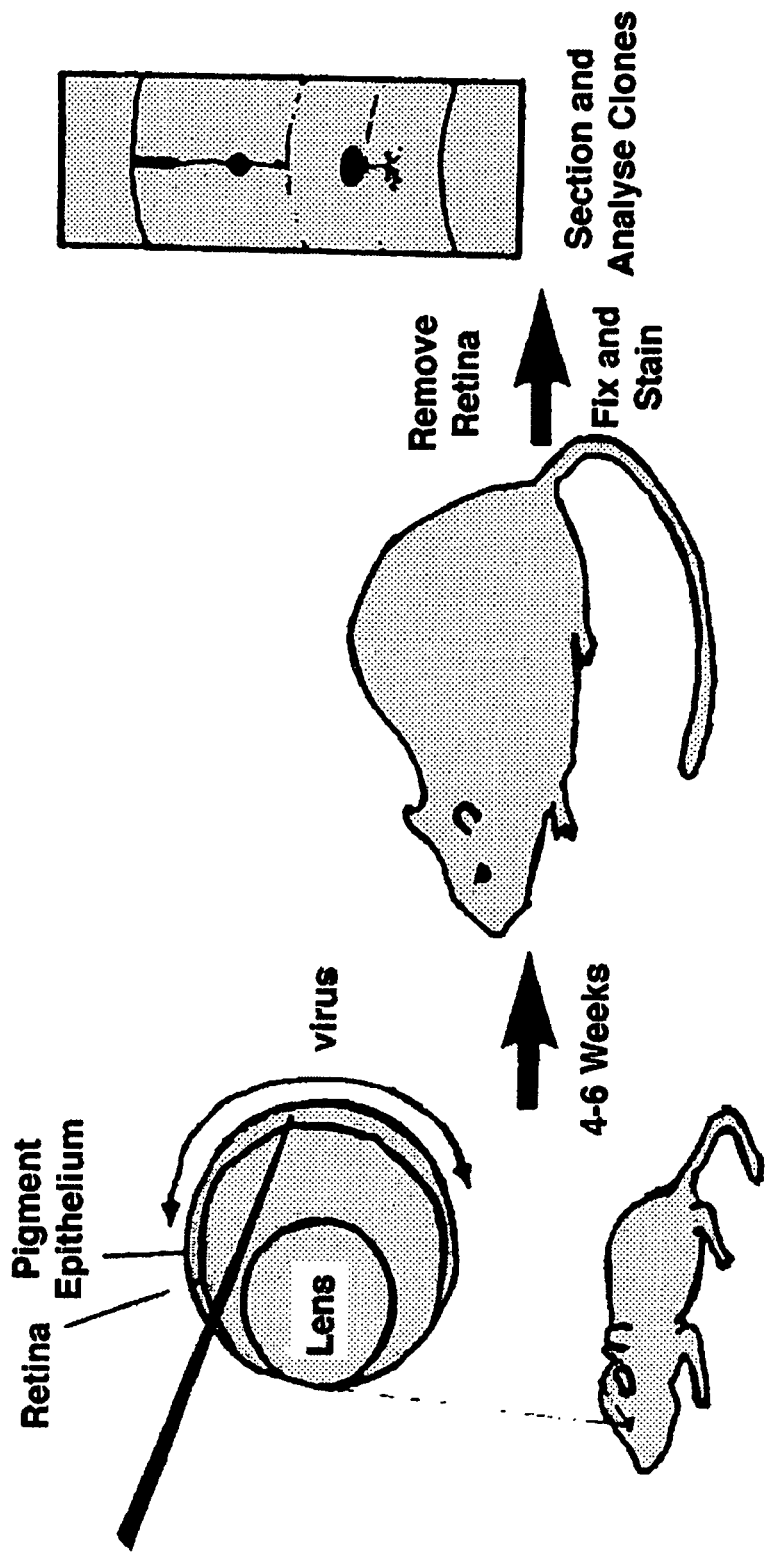
FIG. 2 is a view showing summary of a virus infection test. In the figure, "Retina" represents retina, "Pigment Epithelium" represents retinal pigment epithelium, "virus" represents a range infected with a virus, "Remove Retina" represents extraction of retina, "Fix and Stain" represents tissue fixation and staining, and "Section and Analyse Clones" represents a frozen section and its analysis.

Then, as shown in FIG. 2, an infant rat immediately after birth (0 day after birth) was subjected to low temperature anesthesia, and a skin covering an ocular part was excised with operation scissors. 5 μl of the virus solution of a control virus vector or an Otx2 virus vector was injected under a retina of an infant rat using an injection needle (manufactured by Hamilton). After injection, an infant rat was warmed at 37° C. for 20 minutes to recover a body temperature, returned to a breeding cage of a mother rat, and subsequently reared for 4 to 6 weeks.

A rat grown to adult was subjected to euthanasia by administering sodium pentobarbital. Eyes were isolated from the rat, and retina was removed. The retina was fixed overnight at 4° C. with a 4% paraformaldehyde solution. A 4% paraformaldehyde solution was exchanged with PBS (Phosphate Buffer Saline), and a fixed retina was washed. This fixation/washing operation was repeated three times. Then, retina fixed with a 4% paraformaldehyde solution was thermally treated at 65° C., and endogenous alkaline phosphatase was inactivated. Thermally treated retina was stained with an alkaline phosphate staining solution (room temperature, 3 hours) to stain only a retinal cell infected with the aforementioned virus in blue purple. This stained retina was fixed again overnight with a 4% paraformaldehyde solution, washed with PBS, then, immersed overnight in 30% sucrose/PBS solution overnight, transferred into an OTS compound (Sakura Finetek) liquid, and a frozen block of retina was prepared on dry ice. An about 30 μm frozen section was prepared from a frozen block using a frozen section preparing apparatus (Karl Zeis), and this was observed under the optical microscope (Karl Zeis).

Figure 3:
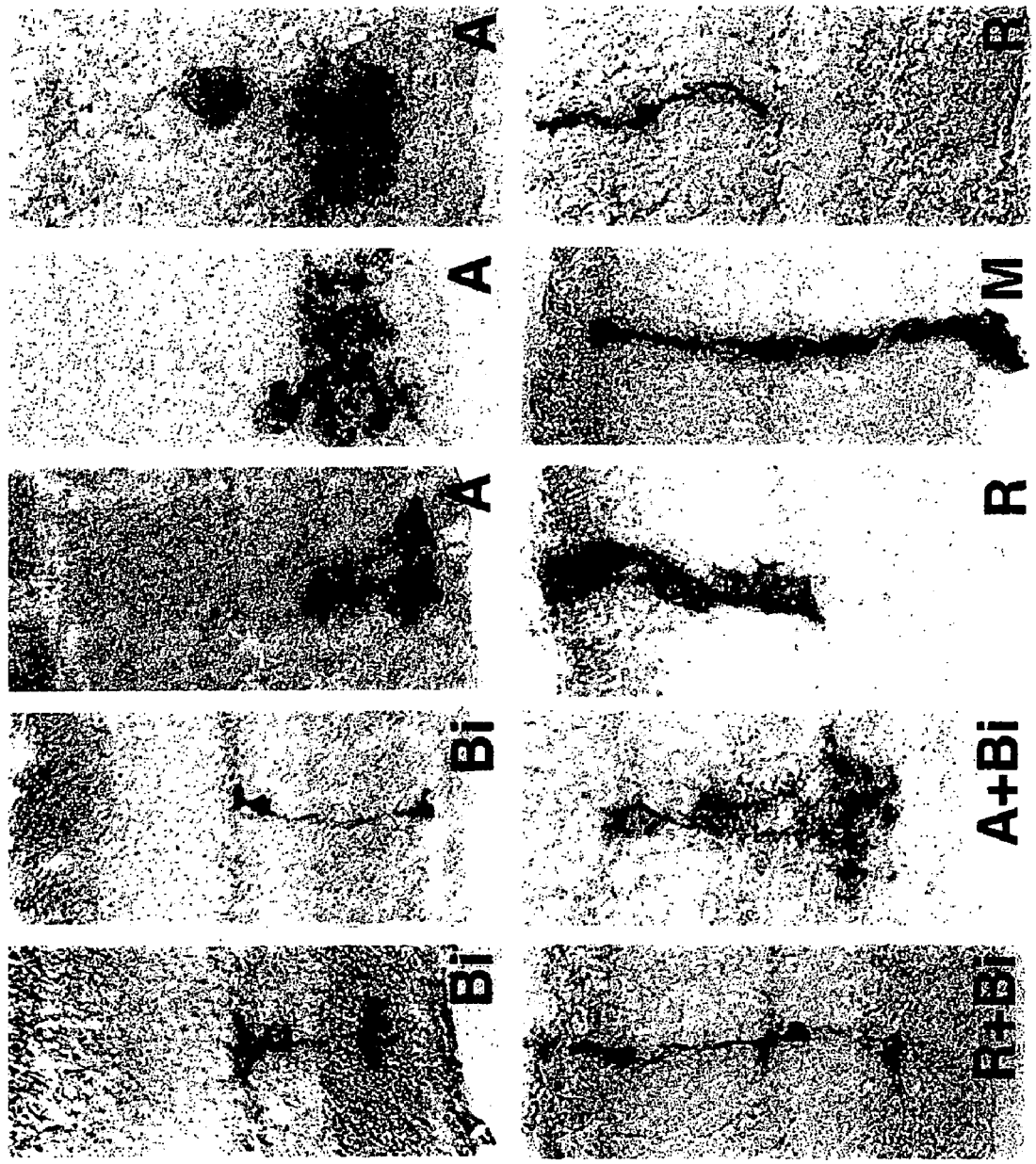
FIG. 3 is a view showing an example of a retinal frozen section image after alkaline phosphatase staining. In the figure, "Bi" represents a bipolar cell, "A" represents an amacrine cell, "R" represents a retinal photoreceptor cell, "M" represents a Muller glial cell, "R+Bi" represents a retinal photoreceptor cell and a Muller glial cell, and "A+Bi" represents an amacrine cell and a bipolar cell.
Figure 4:
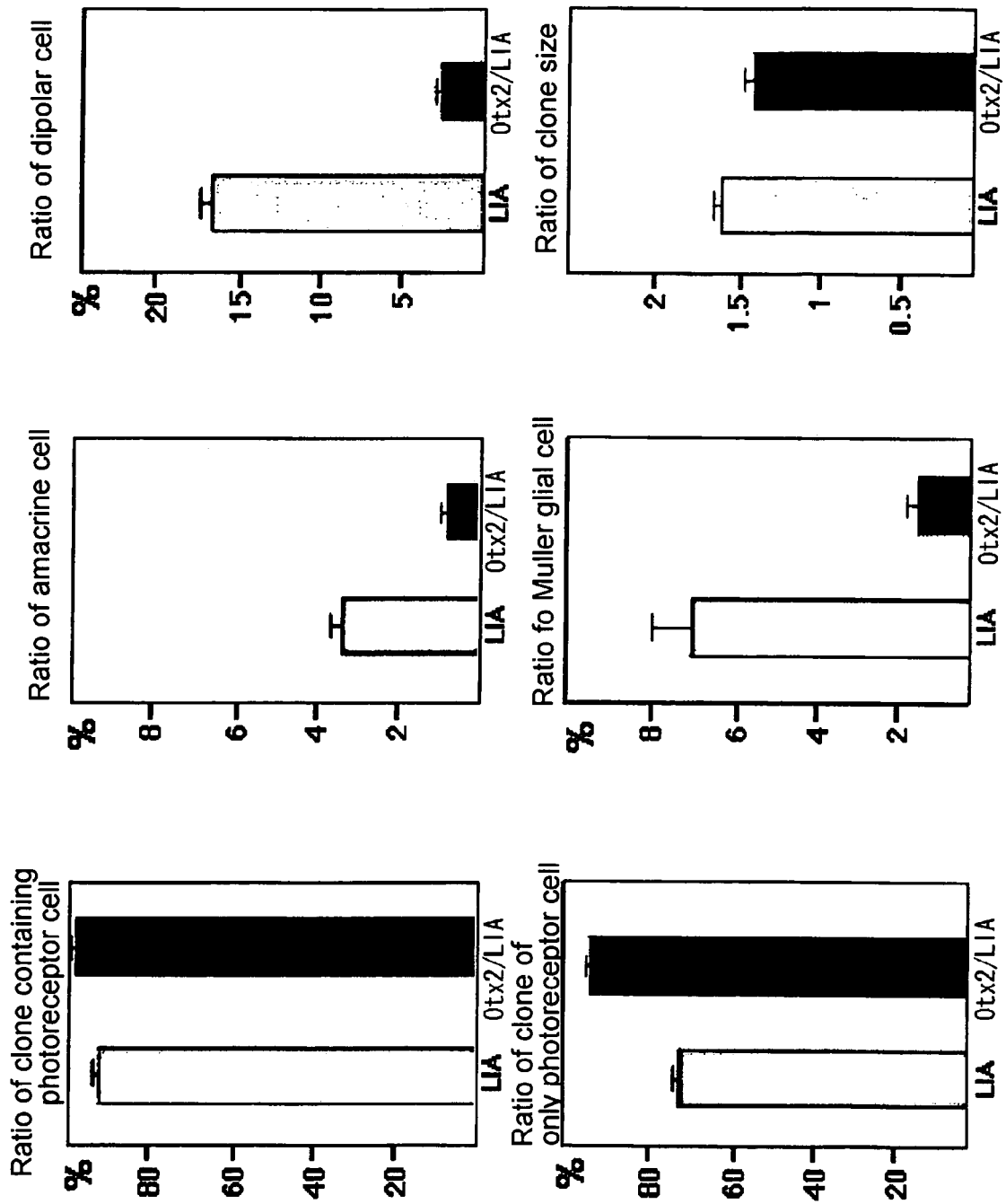
FIG. 4 is a view showing an existence ratio of each of cells differentiated from a retinal stem cell infected with a control virus vector (LIA) or an Otx2 virus vector (Otx2/LIA), relative to a total cell number in a microscopic one field.

A kind of each cell of retina was identified by its form and position (see FIG. 3). This was performed three times by an independent test. An existence rate of each cell relative to all cell number seen in one field is shown in FIG. 4. When an Otx2 virus vector was introduced into a retinal stem cell (or retinal precursor cell), the number of retinal photoreceptor cells was increased by about 10% as compared with the case where a control virus vector was introduced. From this, it was seen that, by expression of an Otx2 gene, differentiation from a retinal stem cell into a bipolar cell, an amacrine cell and a Muller glian cell was strongly suppressed, and almost of retinal stem cells are differentiated into retinal photoreceptor cells.

From the above result, it was confirmed that, by introducing an Otx2 gene into an undifferentiated retinal stem cell, and expressing an Otx2 gene in the cell, it is possible to effectively differentiate an undifferentiated retinal stem cell of a rat into a retinal photoreceptor cell.

INDUSTRIAL APPLICABILITY

The present protein or the present DNA can be utilized in a drug for the purpose of preventing, treating or suppressing progression of retinal diseases such as retinitis pigmentosa, senile macular degeneration, diabetic retinopathy, retinal detachment, glaucoma and retinal vessel occlusion. Further, since abnormality of an Otx2 gene leads to structural or functional abnormality of a retinal photoreceptor cell, by detecting abnormality of an Otx2 gene or degeneration or reduction in expression of an Otx2 protein, this can be utilized in diagnosis of the aforementioned disease.

The invention claimed is:

1. A method for inducing differentiation into a retinal photoreceptor cell and suppressing differentiation into a bipolar cell, an amacrine cell and a Muller glia cell, which method comprises:
   introducing a DNA or an RNA encoding an Otx2 protein into an eye ball tissue-derived cell, an embryonic stem cell, a neural stem cell or a neural precursor cell; and
   culturing the resulting cell containing the DNA or RNA encoding an Otx2 protein to express an Otx2 protein, or increase an amount of expression of an Otx2 protein,
   wherein the Otx2 protein is a protein having the amino acid sequence of SEQ ID NO:1, SEQ ID NO:3 or SEQ ID NO:5.

2. The method according to claim 1, which method comprises:
   introducing a DNA or an RNA encoding an Otx2 protein into an eye ball tissue-derived cell or an embryonic stem cell; and
   culturing the resulting cell containing the DNA or RNA encoding an Otx2 protein to express an Otx2 protein, or increase an amount of expression of an Otx2 protein,
   wherein the Otx2 protein is a protein having the amino acid sequence of SEQ ID NO:1, SEQ ID NO:3 or SEQ ID NO:5.

3. The method according to claim 2, wherein the eye ball tissue-derived cell is a cell selected from the group consisting of a retinal cell, a retinal stem cell, a retinal precursor cell, a corpus ciliare cell, a corpus ciliare epithelial cell, a retinal pigment epithelial cell and an iris cell.

4. The method according to claim 1, which method comprises:
   introducing a DNA or an RNA encoding an Otx2 protein and a nucleic acid encoding a retinal specific homeobox protein selected from the group consisting of Crx, Chx10, Pax6 and Rax into an eye ball tissue- derived cell, an embryonic stem cell, a neural stem cell or a neural precursor cell; and
   culturing the resulting cell containing the DNA or RNA encoding an Otx2 protein to express an Otx2 protein, or increase an amount of expression of an Otx2 protein,
   wherein the Otx2 protein is a protein having the amino acid sequence of SEQ ID NO:1, SEQ ID NO:3 or SEQ ID NO:5.

5. The method according to claim 1, which method comprises:
   introducing a DNA or an RNA encoding an Otx2 protein into an eye ball tissue-derived cell, an embryonic stem cell, a neural stem cell or a neural precursor cell using an adenovirus vector, a retrovirus vector, an adeno-associated virus vector, lipofection or electroporation; and
   culturing the resulting cell containing the DNA or RNA encoding an Otx2 protein to express an Otx2 protein, or increase an amount of expression of an Otx2 protein,
   wherein the Otx2 protein is a protein having the amino acid sequence of SEQ ID NO:1, SEQ ID NO:3 or SEQ ID NO:5.

6. The method according to claim 1, which method comprises:
   introducing a DNA or an RNA encoding an Otx2 protein into an eye ball tissue-derived cell, an embryonic stem cell, a neural stem cell or a neural precursor cell; and
   culturing the resulting cell containing the DNA or RNA encoding an Otx2 protein in the presence of retinoic acid and serum to express an Otx2 protein, or increase an amount of expression of an Otx2 protein,
   wherein the Otx2 protein is a protein having the amino acid sequence of SEQ ID NO:1, SEQ ID NO:3 or SEQ ID NO:5.

* * * * *